(12) United States Patent
Xiang et al.

(10) Patent No.: US 11,714,211 B2
(45) Date of Patent: Aug. 1, 2023

(54) ESTIMATING SOIL PROPERTIES WITHIN A FIELD USING HYPERSPECTRAL REMOTE SENSING

(71) Applicant: CLIMATE LLC, Saint Louis, MO (US)

(72) Inventors: Haitao Xiang, Chesterfield, MO (US); Xianyuan Yang, Pleasanton, CA (US); Nick Koshnick, San Francisco, CA (US); Nick Cisek, San Francisco, CA (US)

(73) Assignee: CLIMATE LLC, Saint Louis, MO (US)

( * ) Notice: Subject to any disclaimer, the term of this patent is extended or adjusted under 35 U.S.C. 154(b) by 100 days.

(21) Appl. No.: 17/243,447

(22) Filed: Apr. 28, 2021

(65) Prior Publication Data

US 2021/0255362 A1    Aug. 19, 2021

Related U.S. Application Data

(63) Continuation of application No. 16/921,489, filed on Jul. 6, 2020, now Pat. No. 10,996,373, which is a
(Continued)

(51) Int. Cl.
*G01V 99/00* (2009.01)
*G01N 21/359* (2014.01)
(Continued)

(52) U.S. Cl.
CPC ............ *G01V 99/005* (2013.01); *A01B 76/00* (2013.01); *G01N 21/31* (2013.01); *G01N 21/359* (2013.01);
(Continued)

(58) Field of Classification Search
CPC .. G01V 99/05; G01N 21/359; G01N 33/0098; G01N 33/24
(Continued)

(56) References Cited

U.S. PATENT DOCUMENTS 4,492,111 A * 1/1985 Kirkland ................ G01N 33/24
73/9
5,668,719 A    9/1997 Bobrov
(Continued)

FOREIGN PATENT DOCUMENTS

CN    103941254 A    7/2014
EP    2196085 A2    6/2010
(Continued)

OTHER PUBLICATIONS

Ethington, U.S. Appl. No. 14/846,454, filed Sep. 4, 2015, Office Action, dated Jun. 27, 2019.
(Continued)

*Primary Examiner* — Bo Fan
(74) *Attorney, Agent, or Firm* — Harness, Dickey & Pierce, P.L.C.

(57) ABSTRACT

A method for building and using soil models that determine soil properties from soil spectrum data is provided. In an embodiment, building soil model may be accomplished using soil spectrum data received via hyperspectral sensors from a land unit. A processor updates the soil spectrum data by removing interference signals from the soil spectrum data. Multiple ground sampling locations within the land unit are then determined based on the updated soil spectrum data. Soil property data are obtained from ground sampling at the ground sampling locations. Soil models that correlate the updated soil spectrum data with the soil property data are
(Continued)

created based on the updated soil spectrum data and the soil property data. The soil models are sent to a storage for future use.

19 Claims, 10 Drawing Sheets

Related U.S. Application Data continuation of application No. 16/456,883, filed on Jun. 28, 2019, now Pat. No. 10,705,253, which is a continuation of application No. 14/866,160, filed on Sep. 25, 2015, now Pat. No. 10,338,272.

(51) Int. Cl.
| | |
|---|---|
| *G01N 33/00* | (2006.01) |
| *G06Q 10/04* | (2023.01) |
| *G06F 30/27* | (2020.01) |
| *A01B 76/00* | (2006.01) |
| *G01N 21/31* | (2006.01) |
| *G01W 1/10* | (2006.01) |
| *G01N 33/24* | (2006.01) |
| *G01N 21/17* | (2006.01) |
| *A01B 79/00* | (2006.01) |
| *G06F 111/06* | (2020.01) |

(52) U.S. Cl.
CPC ........ *G01N 33/0098* (2013.01); *G01N 33/24* (2013.01); *G01W 1/10* (2013.01); *G06F 30/27* (2020.01); *G06Q 10/04* (2013.01); *A01B 79/005* (2013.01); *G01N 2021/1793* (2013.01); *G01N 2021/3155* (2013.01); *G01N 2201/0616* (2013.01); *G01N 2201/129* (2013.01); *G06F 2111/06* (2020.01)

(58) Field of Classification Search
USPC ..... 700/2, 216, 225, 240, 275, 283; 701/532
See application file for complete search history.

(56) References Cited

U.S. PATENT DOCUMENTS

| | | | |
|---|---|---|---|
| 5,796,932 A | 8/1998 | Fox | |
| 6,422,508 B1 | 7/2002 | Barnes | |
| 6,608,672 B1 | 8/2003 | Shibusawa | |
| 6,853,937 B2 | 2/2005 | Shibusawa | |
| 6,937,939 B1 | 8/2005 | Shibusawa | |
| 8,426,211 B1 | 4/2013 | Sridhar | |
| 8,655,601 B1 | 2/2014 | Sridhar | |
| 8,737,694 B2 | 5/2014 | Bredehoft | |
| 9,076,118 B1 | 7/2015 | Mewes | |
| 2002/0133505 A1 | 9/2002 | Kuji | |
| 2002/0183867 A1 | 12/2002 | Gupta | |
| 2005/0027572 A1 | 2/2005 | Goshert | |
| 2005/0234691 A1 | 10/2005 | Singh | |
| 2006/0004907 A1 | 1/2006 | Pape | |
| 2006/0167926 A1 | 7/2006 | Verhey | |
| 2007/0085673 A1 | 4/2007 | Krumm | |
| 2008/0287662 A1 | 11/2008 | Wiesman | |
| 2010/0155156 A1* | 6/2010 | Finkelstein | B25J 5/007 901/1 |
| 2011/0106451 A1 | 5/2011 | Christy | |
| 2011/0137456 A1* | 6/2011 | Koselka | A01B 51/026 701/532 |
| 2012/0016517 A1* | 1/2012 | Holland | A01B 79/005 700/240 |
| 2012/0083907 A1 | 4/2012 | Motavalli | |
| 2012/0101861 A1 | 4/2012 | Lindores | |
| 2013/0018586 A1 | 1/2013 | Peterson | |
| 2013/0144827 A1 | 6/2013 | Trevino | |
| 2013/0173321 A1 | 7/2013 | Johnson | |
| 2013/0174040 A1 | 7/2013 | Johnson | |
| 2013/0322025 A1 | 12/2013 | Friedberg | |
| 2013/0332205 A1* | 12/2013 | Friedberg | G06Q 50/02 705/4 |
| 2014/0012504 A1 | 1/2014 | Ben-Dor | |
| 2014/0012732 A1 | 1/2014 | Lindores | |
| 2014/0067745 A1 | 3/2014 | Avey et al. | |
| 2014/0089045 A1 | 3/2014 | Johnson | |
| 2014/0358486 A1 | 12/2014 | Osborne | |
| 2015/0026023 A1 | 1/2015 | Sirota | |
| 2015/0095001 A1 | 4/2015 | Massonnat | |
| 2015/0237796 A1 | 8/2015 | Celli | |
| 2015/0370935 A1 | 12/2015 | Starr | |
| 2016/0078375 A1 | 3/2016 | Ethington | |
| 2016/0078569 A1 | 3/2016 | Ethington | |
| 2016/0078570 A1 | 3/2016 | Ethington | |
| 2016/0169855 A1 | 6/2016 | Baity | |
| 2017/0122889 A1* | 5/2017 | Weindorf | G01N 33/24 |
| 2019/0317243 A1 | 10/2019 | Xiang | |
| 2020/0183867 A1 | 6/2020 | Ender | |
| 2020/0281133 A1 | 9/2020 | Rowan | |
| 2020/0337212 A1 | 10/2020 | Xiang | |

FOREIGN PATENT DOCUMENTS

| | | |
|---|---|---|
| WO | WO 2009/048341 A1 | 4/2009 |
| WO | WO 2010/128864 | 11/2010 |
| WO | WO2010128864 A1 | 11/2010 |
| WO | WO 2011/064445 A1 | 6/2011 |
| WO | WO 2014/036281 A2 | 3/2014 |
| WO | WO 2014/146719 A1 | 9/2014 |

OTHER PUBLICATIONS

Ethington, U.S. Appl. No. 14/846,659, filed Sep. 4, 2015, Office Action, dated Jun. 12, 2020.
Ethington, U.S. Appl. No. 14/846,659, filed Sep. 4, 2015, Office Action, dated Apr. 30, 2018.
Ethington, U.S. Appl. No. 14/846,659, filed Sep. 4, 2015, Office Action, dated Jan. 31, 2019.
Ethington, U.S. Appl. No. 14/846,659, filed Sep. 4, 2015, Interview Summary, dated Mar. 8, 2021.
Ethington, U.S. Appl. No. 14/846,659, filed Sep. 4, 2015, Interview Sumary, dated Aug. 3, 2018.
Ethington, U.S. Appl. No. 14/846,659, filed Sep. 4, 2015, Final Office Action, dated Nov. 6, 2020.
Ethington, U.S. Appl. No. 14/846,659, filed Sep. 4, 2015, Final Office Action, dated Oct. 5, 2018.
Ethington, U.S. Appl. No. 14/846,659, filed Sep. 4, 2015, Final Office Action, dated May 30, 2019.
Ethington, U.S. Appl. No. 14/846,454, filed Sep. 4, 2015, Interview Summary, dated Jun. 17, 2020.
Ethingon, U.S. Appl. No. 14/846,422, filed Sep. 4, 2015, Office Action, dated Feb. 2, 2018.
Ethington, U.S. Appl. No. 14/846,454, filed Sep. 4, 2015, Office Action, dated Nov. 12, 2020.
Ethington, U.S. Appl. No. 14/846,661, filed Sep. 4, 2015, Final Office Action, dated Dec. 4, 2018.
Ethington, U.S. Appl. No. 14/846,454, filed Sep. 4, 2015, Office Action, dated May 17, 2018.
Ethington, U.S. Appl. No. 14/846,454, filed Sep. 4, 2015, Final Office Action, dated Apr. 1, 2020.
Ethington, U.S. Appl. No. 14/846,454, filed Sep. 4, 2015, Final Office Action, dated Jan. 2, 2019.
Ethington, U.S. Appl. No. 14/846,422, filed Sep. 4, 2015, Office Action, dated Sep. 11, 2019.
Ethington, U.S. Appl. No. 14/846,422, filed Sep. 4, 2015, Office Action, dated Jan. 30, 2019.
Ethington, U.S. Appl. No. 14/846,422, filed Sep. 4, 2015, Notice of Allowance, dated Jan. 14, 2020.
Ethington, U.S. Appl. No. 14/846,422, filed Sep. 4, 2015, Interview Summary, dated Mar. 7, 2019.
Ethington, U.S. Appl. No. 14/846,422, filed Sep. 4, 2015, Final Office Action, dated Aug. 29, 2018.

(56) References Cited

OTHER PUBLICATIONS

Ethington, U.S. Appl. No. 14/846,422, filed Sep. 4, 2015, Final Office Action, dated May 9, 2019.
Ethington, U.S. Appl. No. 14/846,422, filed 069/04/2015, Interview Summary, dated Jun. 4, 2019.
Ethington, U.S. Appl. No. 14/846,454, filed Sep. 4, 2015, Notice of Allowance, dated Apr. 16, 2021.
Xiang, U.S. Appl. No. 14/866,160, filed Sep. 25, 2015, Office Action, dated Jul. 27, 2018.
Xiang, U.S. Appl. No. 14/866,160, filed Sep. 25, 2015, Notice of Allowance, dated Jul. 27, 2018.
Xiang, U.S. Appl. No. 16/921,489, filed Jul. 6, 2020, Office Action, dated Sep. 18, 2020.
Xiang, U.S. Appl. No. 16/921,489, filed Jul. 6, 2020, Notice of Allowance, dated Jan. 13, 2021.
Xiang, U.S. Appl. No. 16/456,883, filed Jun. 28, 2019, Office Action, dated Dec. 12, 2019.
Xiang, U.S. Appl. No. 16/456,883, filed Jun. 28, 2019, Notice of Allowance, dated Mar. 12, 2020.
Xiang, U.S. Appl. No. 14/866,160, filed Sep. 25, 2015, Office Action, dated Sep. 22, 2017.
Xiang, U.S. Appl. No. 14/866,160, filed Sep. 25, 2015, Notice of Allowance, dated Apr. 2, 2019.
Xiang, U.S. Appl. No. 14/866,160, filed Sep. 25, 2015, Notice of Allowance, dated Jan. 26, 2018.
Ethington, U.S. Appl. No. 14/846,659, filed Sep. 4, 2015, Office Action, dated Dec. 11, 2019.
Xiang, U.S. Appl. No. 14/866,160, filed Sep. 25, 2015, Advisory Action, dated May 14, 2018.
Ethington, U.S. Appl. No. 14/846,659, filed Sep. 4, 2015, Notice of Allowance, dated Apr. 12, 2021.
Ethington, U.S. Appl. No. 14/846,661, filed Sep. 4, 2015, Notice of Allowance, dated May 5, 2021.
Ethington, U.S. Appl. No. 14/846,661, filed Sep. 4, 2015, Interview Summary, dated Jan. 12, 2021.
Ethington, U.S. Appl. No. 14/846,661, filed 096/04/2015, Office Action, dated Jun. 27, 2019.
Ethington, U.S. Appl. No. 14/846,661, filed Sep. 4, 2015, Office Action, dated Oct. 7, 2020.
Ethington, U.S. Appl. No. 14/846,661, filed Sep. 4, 2015, Final Office Action, dated Mar. 27, 2020.
Ethington, U.S. Appl. No. 14/846,661, filed Sep. 4, 2015, Office Action, dated May 17, 2018.
Ethington, U.S. Appl. No. 14/846,661, filed Sep. 4, 2015, Interview Summary, dated May 14, 2020.
Ethington, U.S. Appl. No. 14/846,661, filed Sep. 4, 2015, Interview Summary, dated Feb. 20, 2019.
Xiang, U.S. Appl. No. 14/866,160, filed Sep. 25, 2015, Notice of Allowance, dated Mar. 1, 2019.
Xiang, U.S. Appl. No. 14/866,160, filed Sep. 25, 2015, Corrected Notice of Allowability, dated Jun. 10, 2019.
Australian Claims in application No. 2016328634, dated Jun. 2018, 3 pages.
Ali, et al., "Modeling Managed Grassland Biomass Estimation by Using Multitemporal Remote Sensing Data—A Machine Learning Approach", IEEE 2016 JSTARS, vol. 10, No. 7, pp. 3254-3264, 16pgs.
Brazilian Patent Office, "Office Action" in Patent Application No. 1120170210436, dated Jun. 23, 2020, 2 pages.
Brazil Patent Office, "Office Action" in application No. BR112018013423-6, dated Aug. 25, 2020, 2 pages.
Brazil Patent Office, "Office Action (with translation)" in application No. BR112018005893-9, dated Jul. 28, 2020, 6 pages.
Brazil Patent Office, "Office Action" in Brazilian Patent Application No. 1120170216647, dated Jun. 23, 2020, 2 pages.
Brazil Claims in application No. BR112018013423-6, dated Aug. 2020, 15 pages.
Brazil Claims in application No. BR112018005893-9, dated Jul. 2020, 7 pages.
Ben-Dor E. et al., "Mapping of Several Soil Properties Using DAIS-7915 Hyperspectral Scanner Data—A Case Study Over Clayey Soils in Israel", vol. 23 No. 6 dated Jan. 25, 2002, 25 pages.
Australian Patent Office, "Search Report" in application No. 2016328634, dated Jun. 6, 2018, 3 pages.
Australian Patent Office, "Search Report" in application No. 2016294138, dated Jan. 28, 2020, 4 pages.
Australian Patent Office, "Office Action" in application No. 2015315001, dated May 29, 2020, 5 pages.
Brazilian Claims in Application No. 1120170216647, dated Jun. 2020, 10 pages.
Brazilian Claims in Patent Application No. 1120170210436, dated Jun. 2020, 3 pages.
Australian Claims in application No. 2016294138, dated Jan. 2020, 11 pages.
Australian Claims in application No. 2016244067, dated Jan. 2021, 5 pages.
Australian Claims in application No. 2015315001, dated May 2020, 7 pages.
Argentina Patent Office, "Search Report" in application No. 20150102913, dated Aug. 11, 2020, 5 pages.
Argentina Patent Office, "Search Report" in application No. 20150102910, dated Aug. 11, 2020, 5 pages.
Argentina Patent Office, "Office Action" in application No. 20160100949, dated Dec. 18, 2020, 7 pages.
Argentina Claims in application No. 20160103689, dated Aug. 26, 2020, 8 pages.
Argentina Claims in application No. 20160100949, dated Dec. 2020, 8 pages.
Argentina Claims in application No. 20150102913, dated Aug. 2020, 7 pages.
Argentina Claims in application No. 20150102910, dated Aug. 2020, 6 pages.
Argentina Claims in application No. 20150102910, dated Dec. 9, 2020, 7 pages.
Anderson K. et al., "Remote Sensing of Soil Surface Properties", Process in Physical Geography: An International Review of Geographical Work in the Natural and Env. Sciences vol. 33, Aug. 6, 2009, 18 pgs.
Australian Patent Office, "Examination Report" in application No. 2016244067, dated Jan. 20, 2021, 4 pages.
European Patent Office, "Search Report" in application No. 16849415. 1-111, dated Oct. 17, 2019, 10 pages.
Shi T. et al., "Visible and Near-Infrared Reflectance Spectroscopy, An Alternative for Monitoring Soil Contamination by Heavy Me", Journal of Hazardous Materials, vol. 265, Dec. 7, 2013, 12pgs.
National Institute of Industrial Property, "Substantive Examination", in application No. 20150102912, dated Dec. 18, 2020, 5 pages.
National Institute of Industrial Property, "Report Prior to the Final Decision", in application No. 20150102910, dated Dec. 9, 2020, 4 pages.
Malapela, E-agriculture, "Can Artificial Intelligence Help Improve Agricultural Productivity?" Dec. 19, 2017, 6 pgs.
Liebig et al., "Greenhouse Gas and Mitigation Potential of Agricultural Practices in Northwestern USA and Western Canada", Soil and Tillage Research, vol. 83, Issue 1, dated Aug. 2005, pp. 25-52. 28pgs.
Khedo et al., "PotatoSense: A Wireless Sensor Network System for Precision Agriculture" IST-Africa 2014 Conf Proceedings, IIMC International Information Management Corporation, 11 pages.
India Claims in application No. 201717012614, dated Nov. 2020, 5 pages.
Henderson, Gary, Verification of Long-Term Pavement Performance Virtual Weather Stations: Phase I Report—Accuracy and Reliability of Virtual Weather Stations, dated May 2006, 94 pages.
Ge Y. et al., "Remote Sensing of Soil Properties in Precision Agriculture: A Review", Frontiers of Earth Science; selected Publications from Chinese Universities, vol. 5 No. 3, Jun. 21, 2011, 10 pages.
Fox G. A, et al. "Soil Property Analysis Using Principal Components Analysis, Soil Line, and Regression Models", Soil Science Society of America, vol. 69, dated Nov. 1, 2005, pp. 1782-1788.

(56) References Cited

OTHER PUBLICATIONS

European Patent Office, "Search Report" in application No. PCT/US2015/049466, dated Nov. 9, 2015, 12 pages.
Brazilian Claims in Application No. 1120170047500, dated May 2020, 4 pages.
European Patent Office, "Search Report" in application No. 20162576.1-1222, dated Jul. 2, 2020, 11 pages.
The International Bureau of WIPO, "International Preliminary Report on Patentability", Search Report in application No. PCT/US2016/052622, dated Mar. 27, 2018, 12 pages.
European Patent Office, "Search Report" in application No. 15775530.7-1217, dated Sep. 13, 2018, 6 pages.
European Claims in application No. PCT/US2015/049466, dated Nov. 2015, 5 pages.
European Claims in application No. PCT/US2015/049464, dated Nov. 2015, 7 pages.
European Claims in application No. PCT/2015/049456, dated Nov. 2015, 7 pages.
European Claims in application No. 20162576.1-1222, dated Jul. 2020, 6 pages.
European Claims in application No. 16849415.1-1111, dated Oct. 2019, 4 pages.
European Claims in application No. 15775530.7-1217, dated Sep. 2018, 4 pages.
E-Agriculture, "Can Artificial Intelligence Help Improve Agricultural Productivity", dated Dec. 19, 2017.
Current Claims in application No. PCT/US2016/052622, dated Mar. 2018, 6 pages.
Current Claims in application No. PCT/US2016/052622, dated Dec. 2016, 6 pages.
Brown C. D. et al., "Derivative Preprocessing and Optimal Corrections for Baseline Drift in Multivariate Calibration", Applied Spectroscopy, vol. 54, No. 7, dated Jul. 1, 2000, 14 pages.
Brazilian Patent Office, "Office Action" in Application No. 1120170047500, dated May 19, 2020, 2 pages.
European Patent Office, "Search Report" in application No. PCT/US2015/049464, dated Nov. 9, 2015, 11 pages.

\* cited by examiner

Fig. 2
(a)

200 Mobile Computer Application

- 208 Seeds and Planting Instructions
- 210 Nitrogen Instructions
- 212 Weather Instructions
- 214 Field Health Instructions
- 216 Performance Instructions 206 Digital Map Book 204 Overview and Alert Instructions 202 Account, Fields, Data Ingestion, Sharing Instructions

(b)

220 Cab Computer Application

- 222 Maps - Cab
- 224 Remote View
- 226 Data Collect and Transfer
- 228 Machine Alerts
- 230 Script Transfer 232 Scouting - Cab

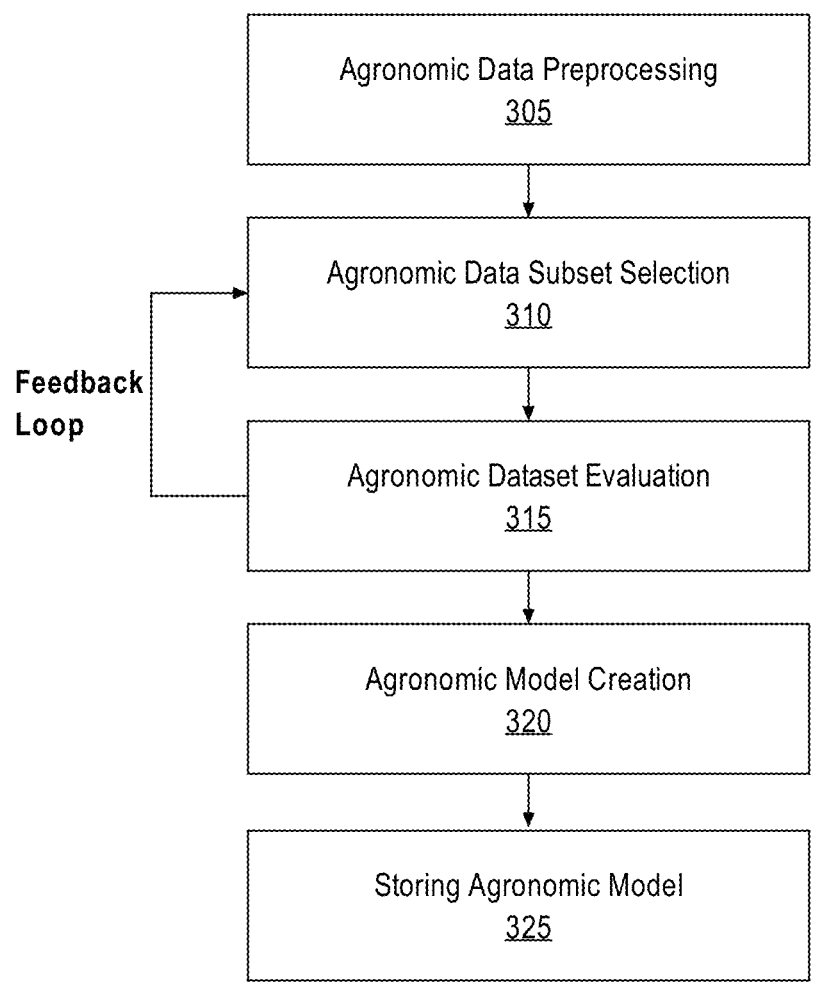

ESTIMATING SOIL PROPERTIES WITHIN A FIELD USING HYPERSPECTRAL REMOTE SENSING

CROSS-REFERENCE TO RELATED APPLICATIONS

This application claims the benefit under 35 U.S.C. § 120 as a continuation of application Ser. No. 16/921,489, filed Jul. 6, 2020, which is a continuation of application Ser. No. 16/456,883, filed Jun. 28, 2019, now U.S. Pat. No. 10,705,253, issued on Jul. 7, 2020, which is a continuation of application Ser. No. 14/866,160, filed Sep. 25, 2015, now U.S. Pat. No. 10,338,272, issued on Jul. 2, 2019. This application is related to, and includes provisional application 62/049,898, filed Sep. 12, 2014, provisional application 62/049,937, filed Sep. 12, 2014, provisional application 62/049,909, filed Sep. 12, 2014, and provisional application 62/049,929, filed Sep. 12, 2014, the entire contents of which are hereby incorporated by reference for all purposes as if fully set forth herein. The applicant(s) hereby rescind any disclaimer of claim scope in the parent application(s) or the prosecution history thereof and advise the USPTO that the claims in this application may be broader than any claim in the parent application(s).

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2019 The Climate Corporation.

FIELD OF THE DISCLOSURE

The present disclosure generally relates to computer systems useful in agriculture. The present disclosure relates more specifically to computer systems that are programmed to use remotely sensed spectral data to provide estimations of soil properties within a field for the purpose of determining soil properties for soil management and to provide location data and/or a soil map with recommendation data relating to taking specific actions on the field, such as planting, nutrient applications, scouting, or implementing sentinel seed technology for the purpose of determining intrafield properties related to crop yield and crop health.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Agricultural production requires significant strategy and analysis. In many cases, agricultural growers, such as farmers or others involved in agricultural cultivation, are required to analyze a variety of data to make strategic decisions before and during the crop cultivation period. In making such strategic decisions, growers rely on spatial information related to intra-field properties to determine crop yields and potential quality of crops. For example, spatial information of soil properties is an important tool to understanding agricultural ecosystems, which can provide information related to healthy soils, adequate nutrient supply for crops, preventing losses of sediments and nutrients from soil, and evaluating the transfer of elements such as carbon from the soil into the atmosphere.

Measuring spatial variability of intrafield properties has traditionally been accomplished through field grid sampling. For example, measuring spatial variability of soil properties is typically accomplished through field grid sampling of soil, where farmers collect soil samples every 1 to 2.5 acres. Those samples are then analyzed to determine different soil properties such as nitrogen, phosphorus and/or potassium levels. This soil analysis procedure is labor intensive, time consuming, and economically expensive.

BRIEF DESCRIPTION OF THE DRAWINGS

In the drawings:

FIG. 2 illustrates two views of an example logical organization of sets of instructions in main memory when an example mobile application is loaded for execution.

FIG. 3 illustrates a programmed process by which the agricultural intelligence computer system generates one or more preconfigured agronomic models using agronomic data provided by one or more data sources.

DETAILED DESCRIPTION

Figure 1:
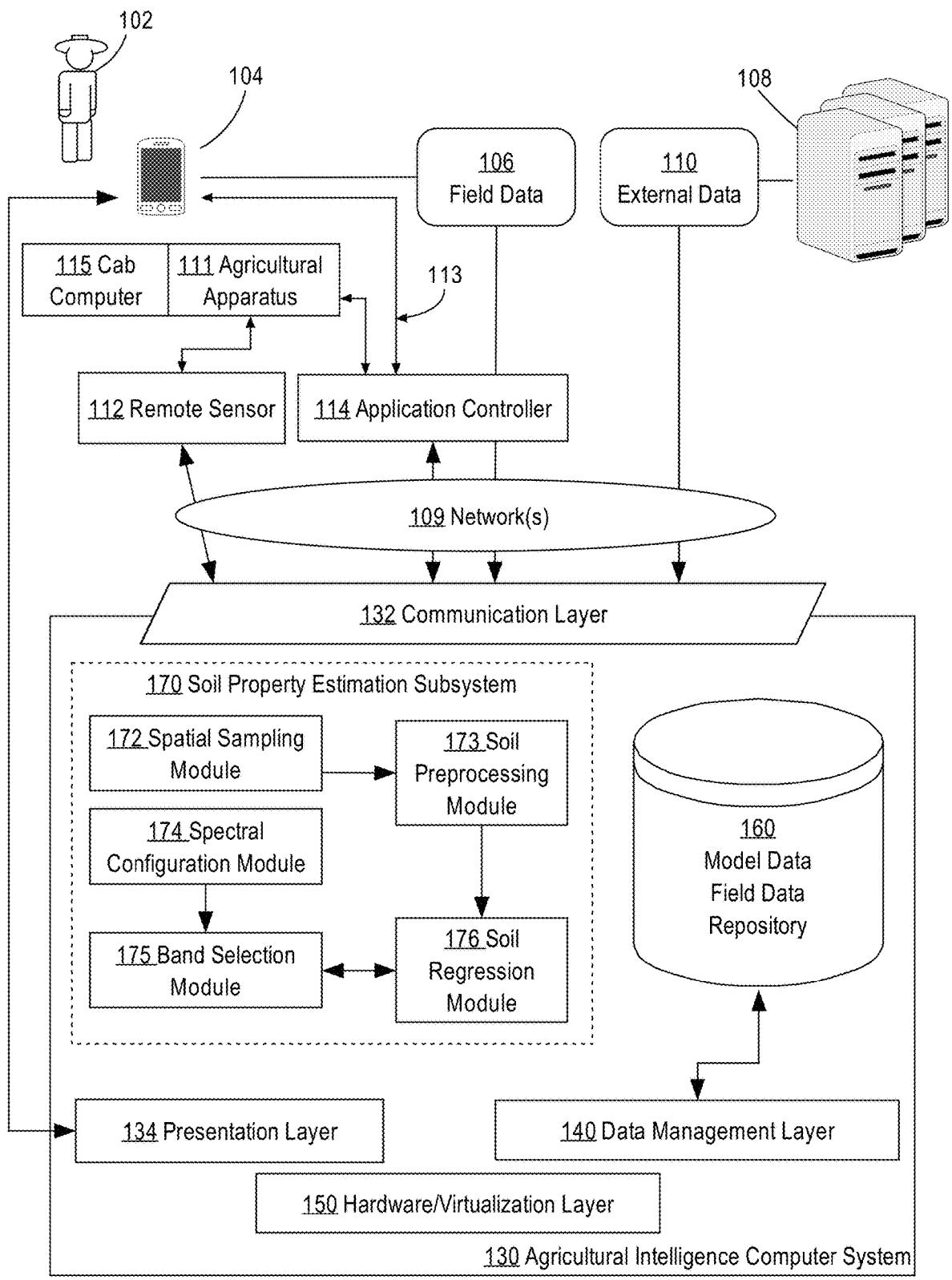
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention. Embodiments are disclosed in sections according to the following outline:

1. GENERAL OVERVIEW
2. EXAMPLE AGRICULTURAL INTELLIGENCE COMPUTER SYSTEM
   2.1 STRUCTURAL OVERVIEW
   2.2. APPLICATION PROGRAM OVERVIEW
   2.3. DATA INGEST TO THE COMPUTER SYSTEM
   2.4 PROCESS OVERVIEW—AGRONOMIC MODEL TRAINING
   2.5 SOIL PROPERTY ESTIMATION SUBSYSTEM
   2.6 IMPLEMENTATION EXAMPLE—HARDWARE OVERVIEW
3. FUNCTIONAL OVERVIEW
   3.1 ESTIMATING INTRA-FIELD SOIL PROPERTIES
   3.2 PRECONFIGURED SOIL MODEL
4. EXTERNAL DATA
   4.1 HYPERSPECTRAL DATA
5. SOIL PROPERTY ESTIMATION SUBSYSTEM FEATURES
   5.1 SOIL PREPROCESSING
   5.2 BAND SELECTION MODULE
   5.3 SOIL REGRESSION MODULE
   5.4 LOCAL SOIL MODEL

1. General Overview

A computer-implemented data processing method for estimating intrafield properties within a field using hyperspectral remotely sensed data is provided. For example, by using hyperspectral remotely sensed data, measuring spatial variability of soil properties can be accomplished without time consuming, labor intensive, and economically expensive physical analysis of individually collected soil samples. In an embodiment, estimating soil properties may be accomplished using a server computer system that receives, via a network, soil spectrum data records that are used to predict soil properties for a specific geo-location. Within the server computer system a soil preprocessing module receives one or more soil spectrum data records that represent a mean soil spectrum of a specific geo-location of a specified area of land. The soil preprocessing module then removes interference signals from the soil spectrum data, creating a set of one or more spectral bands that best represent specific soil properties present. By removing interference signals, the spectral bands are not erroneously skewed from effects such as baseline drift, particle deviation, and surface heterogeneity.

A soil regression module inputs the one or more soil spectral bands and predicts soil property datasets. The soil property datasets are a collection of specific measured soil properties relevant to determining fertility of the soil or soil property levels that may influence soil management at a specific geo-location. The soil regression module then takes the multiple soil property datasets and selects multiple specific soil property datasets that best represent the existing soil properties. Included in the soil property datasets are the multiple soil properties predicted and the spectral band data used to determine the specific soil properties. The soil regression module sends this predicted data to a soil model database.

A spectral configuration module and a band selection module are used to create and calibrate the soil property data models that are used to predict soil properties for a specific geo-location.

Spatial sampling may be implemented to determine optimal ground sampling locations within a specific land unit to provide a representative soil sampling of the entire soil range.

Spatial sampling may also be implemented to determine optimal locations for planting, nutrient applications, scouting, or implementing sentinel seed technology for the purpose of determining intrafield properties related to crop yield and crop health, and these locations may be represented in a soil map or other output.

In an embodiment, the soil property data models may be used to provide input data points of soil compositions including in order to determine nutrient concentration levels of fields, soil composition for determining variable rates of nutrient treatment on fields, and determining soil interpolation maps for specific fields, sub-fields, and other agricultural management zones. In another embodiment, soil property data models may provide soil compositions for different data layers used in determining correlation patterns for soil field mapping. In another embodiment, soil property data models may provide soil compositions of intra-field area when predicting surface soil moisture for one or more fields, sub-fields, and other agricultural management zones. For instance, soil property data models created using the soil regression module may provide correlations between different soil compositions when predicting surface soil moisture. In another embodiment, soil property data models may provide soil compositions for interpreting field sample measurements provided by field probes and Nitrogen/Potassium/Phosphorus sensors. In another embodiment, soil property data models may provide soil compositions for generating a crop prescription that includes a recommended hybrid seed line and population density, where the hybrid seed line and population density are based on the soil composition of the field of interest.

2. Example Agricultural Intelligence Computer System 2.1 Structural Overview

FIG. 1 illustrates an example computer system that is configured to perform the functions described herein, shown in a field environment with other apparatus with which the system may interoperate. In one embodiment, a user 102 owns, operates, or possesses a field manager computing device 104 in a field location or associated with a field location such as a field intended for agricultural activities or a management location for one or more agricultural fields. The field manager computing device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source), (f) pesticide data (for example, pesticide, herbicide, fungicide, other substance or mixture of substances intended for use as a plant regulator, defoliant, or desiccant), (g) irrigation data (for example, application date, amount, source, method), (h) weather data (for example, precipitation, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

An external data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of that might otherwise be obtained from third party sources, such as weather data, and that may actually be incorporated within the system 130.

An agricultural apparatus 111 has one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is an example of such a network that can be installed in combines or harvesters. Application controller 114 is communicatively coupled to agricultural intelligence computer system 130 via the network(s) 109 and is programmed or configured to receive one or more scripts to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a color graphical screen display that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGR-ESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user 102 may be prompted via one or more user interfaces on the user device (served by the agricultural intelligence computer system) to input such information. In an example embodiment, the user 102 may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user 102 may specify identification data by accessing field identification data (provided as shape files or in a similar format) from the U. S. Department of Agriculture Farm Service Agency or other source via the user device and providing such field identification data to the agricultural intelligence computer system.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model data may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

Figure 4:
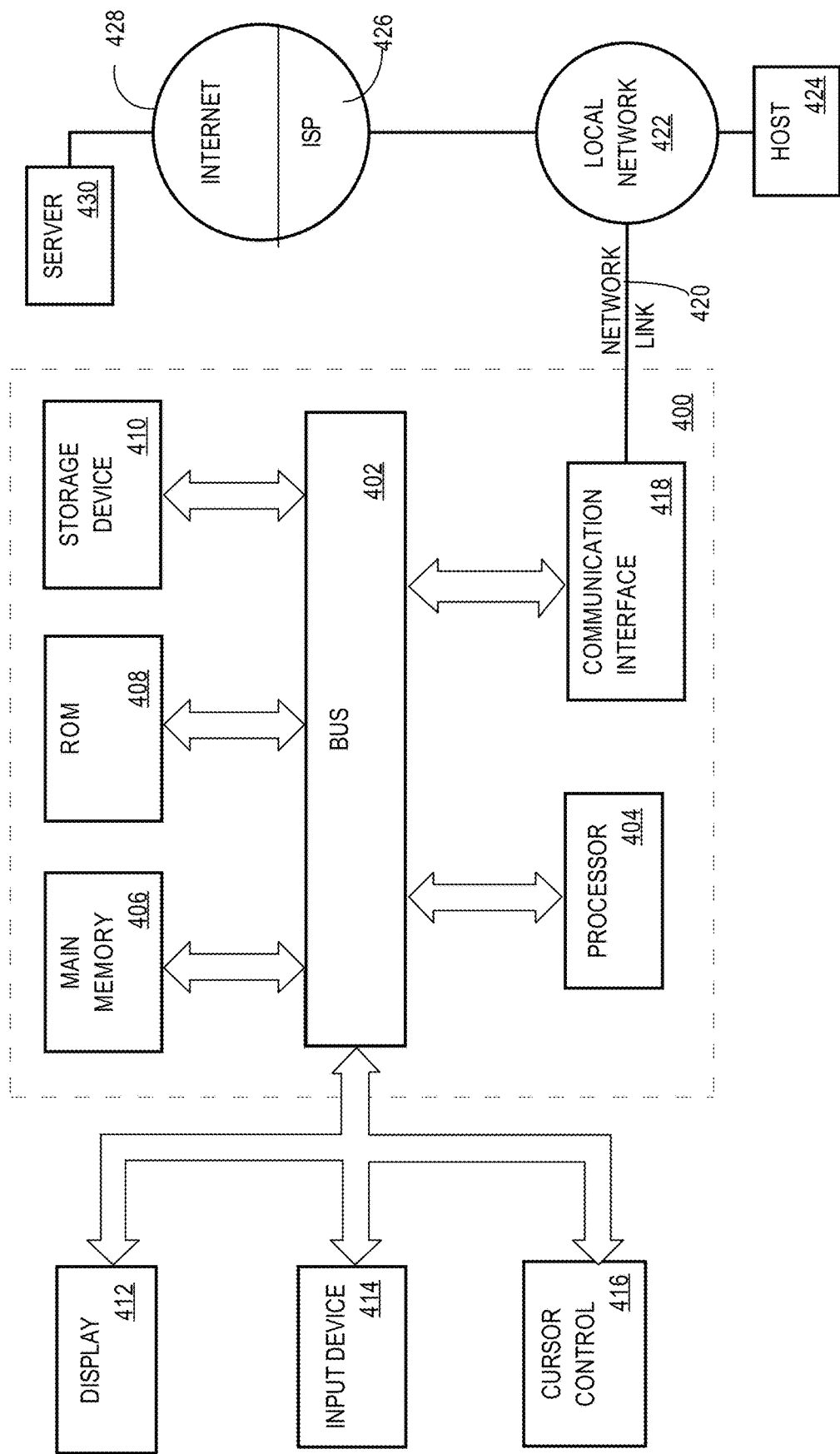
FIG. 4 is a block diagram that illustrates a computer system upon which an embodiment of the invention may be implemented

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility. In some embodiments, external data server computer 108 may actually be incorporated within the system 130.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system 130 independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide server-side functionality, via the network 109 to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML, and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account-fields-data ingestion-sharing instructions 202 are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, external APIs that push data to the mobile application, or instructions that call APIs of external systems to pull data into the mobile application.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 and programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, nitrogen instructions 210 are programmed to provide tools to inform nitrogen decisions by visualizing the availability of nitrogen to crops and to create scripts, including variable rate (VR) fertility scripts. This enables growers to maximize yield or return on investment through optimized nitrogen application during the season. Example programmed functions include displaying images such as SSURGO images to enable drawing of application zones and/or images generated from subfield soil data, such as data obtained from sensors, at a high spatial resolution (such as 1 m or 10 m pixels); upload of existing grower-defined zones; providing an application graph and/or a map to enable tuning nitrogen applications across multiple zones; output of scripts to drive machinery; tools for mass data entry and adjustment; and/or maps for data visualization, among others. "Mass data entry," in this context, may mean entering data once and then applying the same data to multiple fields that have been defined in the system; example data may include nitrogen application data that is the same for many fields of the same grower, but such mass data entry applies to the entry of any type of field data into the mobile computer application 200. For example, nitrogen instructions 210 may be programmed to accept definitions of nitrogen planting and practices programs and to accept user input specifying to apply those programs across multiple fields. "Nitrogen planting programs," in this context, refers to a stored, named set of data that associates: a name, color code or other identifier, one or more dates of application, types of material or product for each of the dates and amounts, method of application or incorporation such as injected or knifed in, and/or amounts or rates of application for each of the dates, crop or hybrid that is the subject of the application, among others. "Nitrogen practices programs," in this context, refers to a stored, named set of data that associates: a practices name; a previous crop; a tillage system; a date of primarily tillage; one or more previous tillage systems that were used; one or more indicators of manure application that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude. In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for other nutrients, such as phosphorus and potassium.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at external data server computer 108 and configured to analyze metrics such as yield, hybrid, population, SSURGO, soil tests, or elevation, among others. Programmed reports and analysis may include yield variability analysis, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at machine sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the agricultural apparatus 111 or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

2.4 Process Overview—Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, and harvesting recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truth that compares predicted results with actual results on a field, such as a comparison of precipitation estimate with a rain gauge at the same location or an estimate of nitrogen content with a soil sample measurement.

FIG. 3 illustrates a programmed process by which the agricultural intelligence computer system generates one or more preconfigured agronomic models using field data provided by one or more external data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise and distorting effects within the agronomic data including measured outliers that would bias received field data values. Embodiments of agronomic data preprocessing may include, but are not limited to, removing data values commonly associated with outlier data values, specific measured data points that are known to unnecessarily skew other data values, data smoothing techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared using cross validation techniques including, but not limited to, root mean square error of leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5 Soil Property Estimation Subsystem

In an embodiment, the agricultural intelligence computer system 130, among other components, includes a soil property estimation subsystem 170. The soil property estimation subsystem 170 is configured to determine intrafield properties, including soil, for specific geo-locations from one or more sources. The soil property estimation subsystem 170 uses external data 110 in the form of different soil spectrum data, which is used to calculate a predicted soil property dataset for a specific geo-location.

The soil spectrum data refers to hyperspectral remotely sensed data that is captured using hyperspectral sensors. Hyperspectral sensors collect images that represent specific continuous spectral bands. A spectral band is a wavelength range of the electromagnetic spectrum. Spectral band analysis can determine different types of soil data or soil properties such as physical, chemical, and biological properties. Physical soil properties may include, but are not limited to, texture, compaction, and water retention. Chemical soil properties may include, but are not limited to, organic matter (OM), electrical conductivity (EC), cation exchange capacity (CEC), pH, moisture content, and content of nutrients such as nitrogen, phosphorus, potassium, calcium, magnesium, zinc, and sodium. Biological soil properties may include, but are not limited to, the amount of respiration, pathogens, microbes, and enzymes. These properties are known to have a significant effect on crop growth. A detailed explanation of hyperspectral data is discussed in the 4.1 HYPERSPECTRAL DATA section herein.

In an embodiment, the external data server computer 108 may store soil spectrum data collected from aerial sensors affixed to satellites, airplanes, and drones. The agricultural intelligence computer system 130 may retrieve external data 110 including soil spectrum data, related to a specific geo-location and time, on-demand and process the soil spectrum data to produce a predicted soil property dataset. Alternatively, the agricultural intelligence computer system 130 may store previously retrieved external data 110 in the model and field data repository 160 for future data processing.

In an embodiment, the soil property estimation subsystem 170 comprises a set of logic modules that are programmed or configured to transform the raw soil spectrum data into predicted soil property datasets. In one embodiment, the soil property estimation subsystem 170 comprises a soil preprocessing module 173 coupled to a soil regression module 176, which is coupled to the model and field data repository 160. A spectral configuration module 174 is coupled to a band selection module 175 and to the model and field data repository 160 for the purposes of creating and tuning new soil data models or updating current soil data models for a specific geo-location. A spatial sampling module 172 is coupled to the soil preprocessing module 173 for the purposes of determining ground sample locations within a specified area based upon soil spectrum data provided by the soil preprocessing module 173. In an embodiment, the spatial sampling module 172 can be used to determined optimal ground sampling locations within a specific land unit to provide a representative soil sampling of the entire soil range. In an embodiment, the spatial sampling module also can be used to determine optimal locations for planting, nutrient applications, scouting, or implementing sentinel seed technology for the purpose of determining intrafield properties related to crop yield and crop health.

In an embodiment, the soil preprocessing module 173 is programmed or configured to receive the soil spectrum data. In an embodiment, soil spectrum data consists of raw data acquired from hyperspectral sensors that scan specific geo-locations. The raw data may be obtained programmatically from government databases, commercial sources with published APIs, or directly from sensing apparatus such as satellites, aircraft, drones, other agricultural machines and handheld instruments with sensing capabilities, or stationary equipment such as buildings, architectural frames, or agricultural implements including seed planters, seed drills, fertilization application tools, or tillage tools planter boxes with sensing capabilities. In embodiments in which the sensors are affixed to an agricultural implement, the sensors may be affixed to a ground-engaging portion (e.g., row unit) of the implement and may be disposed to sense surface soil and/or subsurface soil that has been exposed by operation of the agricultural implement (e.g., by the opening of a planting furrow). The soil spectrum data may be collected by the external data server computer 108 locally or by issuing API calls or web services calls over networks to locations that have been exposed or published by the sensors. For example, an agricultural machine (e.g., combine, tractor, cultivator, plow, subsoiler, sprayer or other machinery used on a farm to help with farming) may be coupled one or more sensors that capture soil spectrum data. Some agricultural machines, such as tractors, may be coupled to a sensing device via an attachment or a towing mechanism. Handheld instruments may also be used. Such instruments may be comprised of a soil testing probe, soil testing system, or traditional field grid sampling system that may involve manually obtaining soil cores from multiple locations in a field. Example instruments are described in provisional application 62/110,405, the entire contents of which are hereby incorporated by reference for all purposes as if fully set forth herein.

In an embodiment, hyperspectral sensor measurements from air, space, or other environments that contribute to noise in the data, stored in the external data server computer 108, may have variations in spectral data that may be attributed to viewing angle, changes in illumination, soil roughness, and low signal-to-noise ratios. Similarly, hyperspectral sensor measurements from ground vehicles, stationary fixtures, and handheld devices, stored in external data server computer 108 may have variations in spectral data attributed to viewing angle, changes in illumination, soil roughness, and low signal-to-noise ratios. In order to reduce interference, the soil preprocessing module 173 is configured to apply one or more preprocessing functions to the raw soil spectrum data. For example, preprocessing functions may incorporate calculating derivate values for a set of moving averages over a particular range of soil spectra. Embodiments of preprocessing functions are discussed on the 5.1 SOIL PREPROCESSING section herein.

The soil preprocessing module 173 is programmed or configured to send the soil spectral bands to the soil regression module 176. The soil preprocessing module 173 removes interference signals from the soil spectrum data to produce soil spectral bands that are a combination of one or more spectral bands from the soil spectrum data. The soil regression module 176 is programmed to use machine learning (e.g., chemometric) techniques to extract soil properties using a preconfigured soil model. The spectral bands received from the soil preprocessing module 173 are inputted into a preconfigured soil model that is programmed to determine relevant soil properties related to the soil spectrum data.

In an embodiment, the band selection module 175 and the spectral configuration module 174 are programmed to determine preferred subsets of soil spectral bands from one or more measured geo-locations. The preferred subsets of soil spectral bands for one or more measured geo-locations are then inputted into the soil regression module 176 in order to produce a preconfigured soil model under program control. A preconfigured soil model is a soil model based upon one or more measured regions that may be used as a global model for predicting future soil properties for measured soil spectrum data from a specific geo-location. Data from the one or more measured regions includes, but is not limited to, measured hyperspectral data and previously measured physical soil samples, referred to as ground truth. For example, the preconfigured soil model may be based on several measured crop fields spanning multiple regions of the mid-west of the United States. The soil regression module 176 is programmed to use the preconfigured soil model may then be used to predict soil properties from future soil spectrum data measured from fields within the mid-west of the United States. In an embodiment, preconfigured soil models may be configured to be applicable to soil spectrum data measured from geo-locations within a defined area ranging from specific counties, states, and nations.

In an embodiment, the measured soil spectrum data used to identify preferred subsets of soil spectral bands may include a measured range from 400 nanometers (nm) to 2500 nm. However, certain sub-regions within the soil spectrum data may be more useful for specific soil property prediction than others for specific soil properties. Therefore the band selection module 175 creates randomly generated spectral band combinations and evaluates which spectral band combinations are more useful than others. A spectral band combination is a set of smaller spectral bands chosen from the soil spectrum data. The band selection module 175 creates a subset of preferred soil spectral band combinations to use during soil property prediction. The band selection module 175 is more effective in determining useful soil spectral band combinations when it incorporates historical soil spectral band combinations into the combination creation process. A spectral configuration module 174 is a module that retrieves historical soil spectral band combinations from previous soil property prediction sessions. The purpose of the spectral configuration module 174 is to function as a feedback loop where previously successful soil property predictions and their associated with spectral band combinations, stored in the model and field data repository 160, are used to influence the creation of an initial soil spectral band combination set done by the band selection module 175.

Further description of the band selection module 175 is in the 5.2 BAND SELECTION MODULE section herein.

The spectral configuration module 174 is programmed to query soil property datasets from the model and field data repository 160. In an embodiment, the model and field data repository 160 stores preconfigured soil models and previously measured soil properties for which the preconfigured soil models are based upon. The previously measured soil property datasets for a specific geo-location include the soil spectral band combination. The soil regression module 176 evaluates preconfigured soil models and soil spectrum data by programmatically applying multivariate regression techniques to the one or more spectral bands. Multivariate regression techniques include, but are not limited to, a partial least squares regression, principal component regression, ridge regression, lasso regression, and random forest and the mathematical basis and/or algorithms useful to program a computer to implement these regression techniques generally may be found in the literature. In an embodiment, the partial least squares regression method characterizes high leverage orthogonal factors within an observed spectral variance and matches the orthogonal factors to similar factors that describe observed variance within measurements of a corresponding dependent variable. Further description of the partial least squared regression method is in the 5.3 SOIL REGRESSION MODULE section herein.

In addition to the preconfigured soil models, a local soil model may be created to provide a more tailored soil property prediction model using hyperspectral data (e.g., near-proximal hyperspectral data) and physical soil samples collected from specific locations within a specific geo-location. The spatial sampling module 172 determines ground sampling locations within a target area for the purposes of collecting specific physical soil samples that are to be used in local soil model creation. The spatial sampling module 172 receives soil spectrum data from the soil preprocessing module 173 and uses spatial sampling techniques to determine the optimal number of ground sampling collection locations or to determine optimal locations for planting, nutrient applications, scouting, or implementing sentinel seed technology for the purpose of determining intrafield properties related to crop yield and crop health. In an embodiment, the spatial sampling module 172 may be programmed to execute conditional Latin Hypercube sampling to determine the ground sampling locations. Other embodiments may implement different spatial sampling techniques for determining ground sampling locations. Local soil model creation is discussed in detail in the section titled 5.4 LOCAL SOIL MODEL.

In an embodiment, the model and field data repository 160 stores the preferred soil property datasets identified by the soil regression module 176. The spectral configuration module 174, for the purpose of pre-configuring the band selection module 175 for future soil property models, is programmed to query the model and field data repository 160.

2.6 Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Functional Overview 3.1 Estimating Intra-Field Soil Properties

Figure 5A:
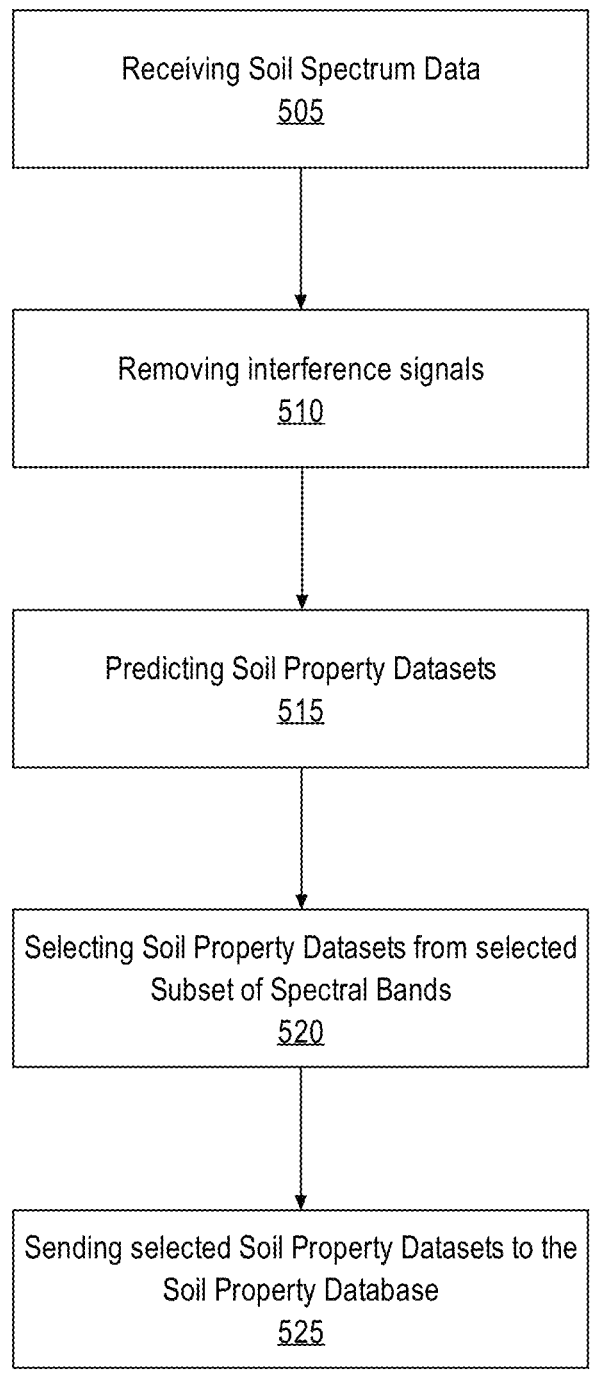
FIG. 5A illustrates a computer-implemented process for receiving soil spectrum data, removing interference signals from the soil spectrum data, and predicting soil property datasets based on the subset of soil spectral bands.

FIG. 5A is a flow diagram that depicts an example computer-implemented process for estimating intra-field soil properties using an existing soil model and soil spectrum data provided by one or more hyperspectral remote sensing servers. For purposes of illustrating a clear example, FIG. 5A is described in connection with certain elements of FIG. 1. However, other embodiments of FIG. 5A may be practiced in many other contexts and references herein to units of FIG. 1 are merely examples that are not intended to limit the broader scope of FIG. 5A. FIG. 5A may serve as an algorithm or instructions for programming the functional elements of the agricultural intelligence computer system 130 to perform the operations that are now described.

At block 505, the soil preprocessing module 173 receives soil spectrum data as external data 110 from the external data server computer 108. In an embodiment, the soil spectrum data includes remotely sensed spectral data for a specific geo-location at a specific time and receiving the soil spectrum data enables the soil preprocessing module 173 to derive soil property datasets for the purposes of evaluating soil properties.

At block 510, the soil preprocessing module 173 removes interference signals from the soil spectrum data using one or more preprocessing methods. For example, if the soil spectrum data values show random spikes depicting light scattering effects because of rough soil, then the soil preprocessing module 173 may determine the standard normal variate for the raw soil spectrum data in order to remove the random spikes. Embodiments of implementing preprocessing methods are further described in the 5.1 SOIL PREPROCESSING section herein.

At block 515, the soil regression module 176 is programmed to create prediction models based off of one or more preconfigured soil models and processed soil spectral bands provided by the soil preprocessing module 173. The soil regression module first retrieves the appropriate preconfigured soil model from the model and field data repository 160. Preconfigured soil models are previously created soil regression models based upon earlier soil spectrum data related to one or more measured geo-locations and preselected spectral bands provided by the band selection module 175. Creating preconfigured soil models is discussed in detail in the 3.2 PRECONFIGURED SOIL MODEL section herein.

Each of the preconfigured soil models created by the soil regression module 176 may comprise instructions, data, or programs that are electronically digitally stored in main memory or nonvolatile storage that is accessible by external systems. The soil regression module 176 may implement different multivariate regression techniques to create the prediction models. Different multivariate techniques include, but are not limited to, partial-least square regression, random forest, principal component analysis, partial least squares, ridge regression, lasso regression, and decision tree statistical procedures and the mathematical basis for programming these techniques may be found in the literature for use in other contexts. By implementing a multivariate regression technique, the soil regression module is able to discover latent variables that may explain variations between the soil spectral bands and predicted soil properties. Multivariate regression techniques are discussed in the 5.3 SOIL REGRESSION MODULE section herein.

At block 520, the soil regression module 176 selects prediction models, including the predicted soil property datasets, based upon a quality threshold. In an embodiment, the soil regression module 176 is programmed to determine the accuracy of the spectral band combinations by evaluating and cross validating the predicted soil property datasets. Different model evaluation techniques include, but are not limited to, root mean square error, mean absolute error, and mean percentage error. Each evaluation technique may implement different types of cross validation methods including, but not limited to, leave-one-out cross validation, k-fold cross validation, and bootstrapping techniques. Evaluation and cross validation techniques are discussed in the 5.3 SOIL REGRESSION MODULE section herein.

At block 525, the soil regression module 176 sends preferred prediction models, including the spectral band combinations used, to the model and field data repository 160. The model and field data repository 160 is then used as a feedback loop by the spectral configuration module 174 and the band selection module 175 to further create and calibrate preconfigured soil models for different geo-locations. In an embodiment, the preferred prediction models, created by the soil regression module 176, may be queried by a field manager computing device 104.

3.2 Preconfigured Soil Model

The soil regression module 176 is programmed to use identified latent variables in a preconfigured soil model to predict soil properties related to the currently received soil spectrum data. Preconfigured soil models are based upon previously processed soil spectrum data that has been previously modeled by the soil regression module 176 and been cross validated to ensure the accuracy of the preconfigured soil model.

Figure 5B:
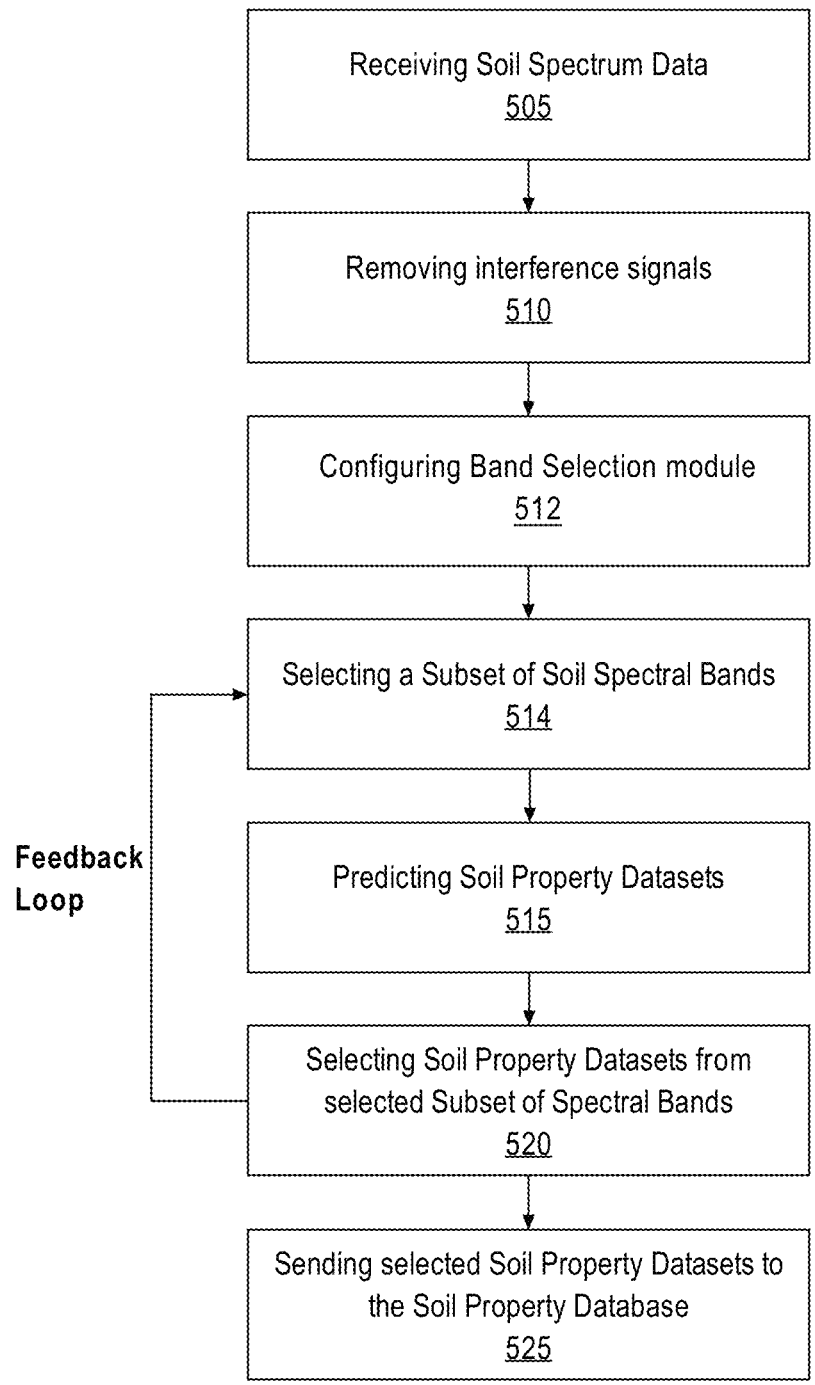
FIG. 5B illustrates a computer-implemented process for generating one or more preconfigured soil models by removing interference signals from the soil spectrum data, selecting a subset of soil spectral bands, and creating a preconfigured soil model based on the subset of soil spectral bands.

FIG. 5B is a flow diagram that depicts an example computer implemented process for generating one or more preconfigured soil models using soil spectrum data provided by one or more hyperspectral remote sensing servers covering a multiple geo-locations and historical soil models stored in the model and field data repository 160. For purposes of illustrating a clear example, FIG. 5B is described in connection with certain elements of FIG. 1. However, other embodiments of FIG. 5B may be practiced in many other contexts and references herein to units of FIG. 1 are merely examples that are not intended to limit the broader scope of FIG. 5B. FIG. 5B may serve as an algorithm or instructions for programming the functional elements of the agricultural intelligence computer system 130 to perform the operations that are now described.

At block 505, the soil preprocessing module 173 receives soil spectrum data as external data 110 from the external data server computer 108. As discussed in FIG. 5A, the soil spectrum data may include remotely sensed spectral data for specific geo-locations at a specific time and receiving the soil spectrum data enables the soil preprocessing module 173 to derive soil property datasets for the purposes of evaluating soil properties.

At block 510, the soil preprocessing module 173 removes interference signals from the soil spectrum data using one or more preprocessing methods as discussed in the 5.1 SOIL PREPROCESSING section herein.

At block 512, the spectral configuration module 174 configures the band selection module 175 for determining a subset of spectral band combinations to be used in creating a preconfigured soil model. The band selection module 175 may implement different band selection techniques, including but not limited to, random band selection that is influenced by historical band information in order to search for subsets of spectral bands. The spectral configuration module 174 queries historical band information stored in the model and field data repository 160. The spectral configuration module 174 uses the historical band information to preselect a set of spectral bands from which the band selection module 175 begins its random selection process.

The processing effort required by the band selection module 175 and the soil regression module 176 may be significant when the initial set of measured spectral bands is large. Using large spectral band sets also leads to complex models and the possibility of identifying several latent variables that provide little explanation for variations between the soil spectrum data and predicted soil properties. By removing spectral bands that are not useful in determining latent variables, the soil regression module 176 is programmed to form simpler and more accurate models. Historical band information retrieved by the spectral configuration module 174 assists in removing spectral bands that provide little use in determining latent variables.

At block 514, the band selection module 175 selects a subset of spectral band combinations. Band selection techniques may include, but are not limited to, genetic algorithm method, all subset models method, sequential search method, stepwise regression method, particle swarm optimization method, and ant colony optimization method. A band selection method then iteratively selects subsets of spectral bands and evaluates the selected spectral band combination. Approaches to implementing the selection of subsets of spectral band combinations are discussed in the 5.2 BAND SELECTION MODULE section herein.

At block 515, the soil regression module 176 creates preconfigured soil models based upon the subset of spectral band combinations provided by the band selection module 175. The soil regression module 176 implements different multivariate regression techniques to create the preconfigured soil models. In an embodiment, the soil regression module 176 implements multivariate regression techniques, using the subset of spectral band combinations, on the soil spectrum data.

At block 520, the soil regression module 176 selects preconfigured soil models that meet a defined quality threshold. In an embodiment, the soil regression module 176 is programmed to determine the accuracy of the spectral band combinations using cross validation techniques. If one or more preconfigured soil models exceed the quality threshold based upon the cross validation, then the soil regression module 176 stores the preconfigured soil model in the model and field data repository 160 (block 525) for later soil property predictions. If however, the one or more baseline models do not meet the defined quality threshold, the spectral band combinations used to create the preconfigured soil models are sent back to the band selection module 175 for further selection analysis. This serves as a feedback loop for the iterative process of the band selection module 175. The band selection module 175 then repeats block 514 in order to select band combinations that may discover more meaningful latent variables. Details on the process of selecting spectral band combinations are discussed in the 5.2 BAND SELECTION MODULE section.

At block 525, the soil regression module 176 sends preferred prediction models, including the spectral band combinations used, to the model and field data repository 160. The model and field data repository 160 may then be accessed by the soil regression module 176 for future model and soil property determination.

4. External Data 4.1 Hyperspectral Data

Hyperspectral data refers to imaging narrow spectral bands over a contiguous spectra range. The resulting images are reflectance measurements of a specific area over a specified wavelength band. In an embodiment, the measured wavelength band may span from 400 nm to 2500 nm. Reflectance is the percentage of light striking and reflecting back from a soil. Some materials reflect certain wavelengths of light, while others absorb the same wavelengths. Therefore patterns of reflectance across multiple wavelengths can uniquely identify certain materials. Hyperspectral remote sensing assumes that the spectra of an object represent the linear combination of the absorption features of each chemical or physical constituent weighted by its concentration. Multivariate statistical analysis may be used to relate concentrations of specific constituents to spectral absorption at different bands.

In an embodiment, hyperspectral sensors may be configured to measure reflectance from different altitudes and angles. For instance, hyperspectral sensors affixed to satellites may be calibrated to account for atmospheric correction, whereas hyperspectral sensors affixed to an airplane or drone may require different levels of calibration.

In another embodiment, hyperspectral sensors may be affixed to agricultural machines, such as a combine or tractor, or land vehicles, such as a truck. In this case, the angle and proximity to the soil may require different calibration techniques and may require further data pre-processing to account for interference. In yet another embodiment, hyperspectral sensors may be affixed to stationary structures such as buildings, architectural frames, or planter boxes. In yet another embodiment, handheld instruments, such as a soil testing probe or soil testing system, may be used. Example instruments are described in provisional applications 62/110,405 and 62/154,207, the entire contents of which are hereby incorporated by reference for all purposes as if fully set forth herein.

5. Soil Property Estimation Subsystem Features 5.1 Soil Preprocessing

Embodiments may be programmed with preprocessing methods to remove biases from spectral information. Embodiments of spectral preprocessing methods may include, but are not limited to, data smoothing, spectral derivatives, standard normal variate preprocessing, and absorbance. The following preprocessing methods may be used separately or in conjunction with other preprocessing methods in order to remove and reduce noise and distorting effects within the soil spectrum data.

Specific regions of the measured spectrum may be excluded due to known interference effects. In an embodiment, such interference effects may be attributed to hyperspectral sensing device. For example, a remote hyperspectral sensing device attached to a satellite may experience interference between regions 1300 nm-1450 nm and 1780 nm-2100 nm due to strong water absorption. The soil preprocessing module 173 may be configured to exclude the above regions based upon the specific sensing device. Another hyperspectral sensing device however, may require the exclusion of the region covering 950 nm-1000 nm because of an overlap between the visible near infrared and short wave infrared regions. Other hyperspectral sensing devices may not require any exclusion of ranges. In an embodiment, the soil preprocessing device may be configured to identify ranges to be excluded based upon the hyperspectral sensing device.

In an embodiment, data smoothing using a Savitzky-Golay filter may be used to reduce random noise and narrow spikes from selected spectral bands of the soil spectrum. A smoothed spectral band value is calculated by determining the sum of neighboring bands between a specific range multiplied by pre-calculated convolution coefficients. An example function is:

$$x_{smooth,j} = \sum_{h=-k}^{k} c_h x_{j+h}$$

where $x_j$ is the raw spectrum value at band j, $x_{smooth,j}$ is the smoothed spectrum value at band j, k is the number of neighboring band values at each side of band j, and $c_h$ is the pre-calculated convolution coefficient that depends on the polynomial order set by the number of neighboring band values k.

Further data smoothing techniques may be applied to remove additive and multiplicative effects of noise in order to enlarge the spectral signature of selected bands. In an embodiment a first derivative may be applied to the smoothed spectrum value $x_{smooth,j}$ in order to resolve the effects of peak overlap from neighboring spectral bands, enhance resolution of the spectral band values, and remove linear baseline drift. The first derivative for $x_{smooth,j}$ is calculated as the difference between two spectral points that are a predetermined distance from $x_{smooth,j}$:

$$x'_j = x_{smooth,j+gap} - x_{smooth,j-gap}$$

where $x'_j$ is the first derivative and gap defines a predetermined distance from the spectral band.

In an embodiment, the second derivative may be applied to the smoothed spectrum value $x_{smooth,j}$ in order to remove linear trends as well as linear baseline drift. The second derivative for $x_{smooth,j}$ is calculated as the difference between the first derivative of two spectral points that are at a predetermined distance from $x_{smooth,j}$:

$$x''_j = x'_{j+gap} - x'_{j-gap} = x_{smooth,j+gap} - 2x_{smooth,j} + x_{smooth,j-gap}$$

where $x''_j$ is the second derivative for $x_{smooth,j}$, $x'_j$ is the first derivative, and gap defines a predetermined distance from the spectral band.

In an embodiment, standard normal variate (SNV) pre-processing may be applied to raw spectrum values in order to reduce the disturbing effect of light scattering. The SNV corrected spectrum value may be calculated as follows:

$$x_{snv,j} = (x_j - \bar{x}_j)/s_j$$

where, $x_{snv,j}$ is the corrected spectrum value at band j, $x_j$ is the raw spectrum value at band j, $\bar{x}_j$ is the average spectrum value over a particular sample spectrum, and $s_j$ is the standard deviation over the particular sample spectrum.

In an embodiment, spectral reflectance may be converted to absorbance. Measuring absorbance instead of raw spectral reflectance values may result in more accurate measurements of different molecules in the soil. Spectral reflectance values are converted to absorbance values using the following equation:

$$x_{absorb,j} = \log 1/x_j$$

where, $x_{absorb,j}$ is the absorbance spectrum value at band j.

Combinations of the pre-processing methods discussed above may be programmed in the system of FIG. 1 to be applied separately or in combination in determining different soil properties. In an embodiment, data smoothing methods may be applied to determine the concentration of potassium in a particular soil sample. In an embodiment, the first spectral derivative may be applied to a post-smoothed spectral value to determine concentration of sulfur in the particular soil sample. In another embodiment, the second spectral derivative may be applied to the post-smoothed spectral value to determine concentrations of phosphorus and sodium. In yet another embodiment, the standard normal variate method may be used to determine the concentration of nitrogen and the buffer pH in the particular soil sample. Another embodiment, may apply absorbance transformation to determine the concentration of organic matter, the concentration of cation exchange capacity, the concentration of calcium, and the concentration of magnesium in the particular soil sample.

5.2 Band Selection Module

The band selection module 175 may be programmed or configured to determine a subset of spectral bands combinations that are most useful for specific soil property prediction. Band selection techniques include, but are not limited to, a genetic algorithm method, an all subset models method, a sequential search method, a stepwise regression method, a particle swarm optimization method, and an ant colony optimization method.

In an embodiment, the band selection module 175 may be programmed or configured using a genetic algorithm to search and determine possible spectral band combinations. A genetic algorithm is an adaptive heuristic search algorithm based on evolutionary ideas of natural selection and genetics. The band selection module 175 may be programmed or configured with the technique of random band selection as well as exploiting historical information in order to direct the search for subset of spectral bands. The band selection module 175 may be programmed or configured to perform the steps of selecting an initial population set, generating a set of offspring from the population set, altering the offspring set by introducing mutations, and then evaluating the mutated offspring set to determine which combinations of bands may be useful for specific soil property prediction.

Figure 6:
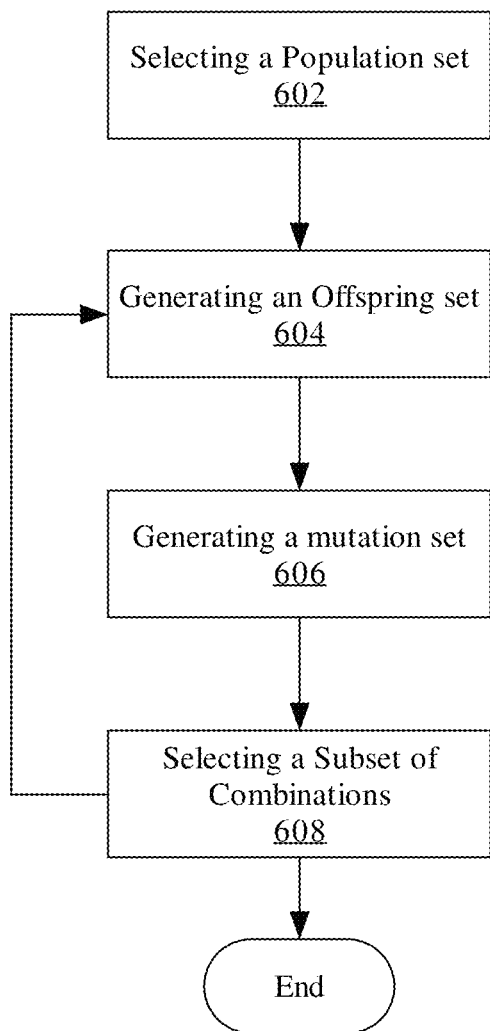
FIG. 6 illustrates a computer-implemented process for selecting a subset of soil spectral bands using a genetic algorithm.

FIG. 6 depicts an embodiment of the genetic algorithm as it applies to determining preferred spectral band combinations. At step 602, the band selection module 175 selects a population set of potential spectral band combinations to evaluate. A population set consists of one or more genetic sequences. A genetic sequence corresponds to an experimental condition which, in this case is a combination of spectral bands across the measured soil spectrum. Here, the genetic sequence is a binary sequence of genes where each gene corresponds to a specific spectral band. The binary sequence of genes make up the entire measured soil spectrum, where a "1" value for a gene may denote that a specific band is considered part of a specific spectral band combination represented by that specific genetic sequence. A "0" value for a gene may denote that a specific band is not part of specific spectral band combination making up the specific genetic sequence. In an embodiment, the population set may consist of a set of 300 genetic sequences. In other embodiments, the number of genetic sequences that make up the population set may vary.

Figure 7:
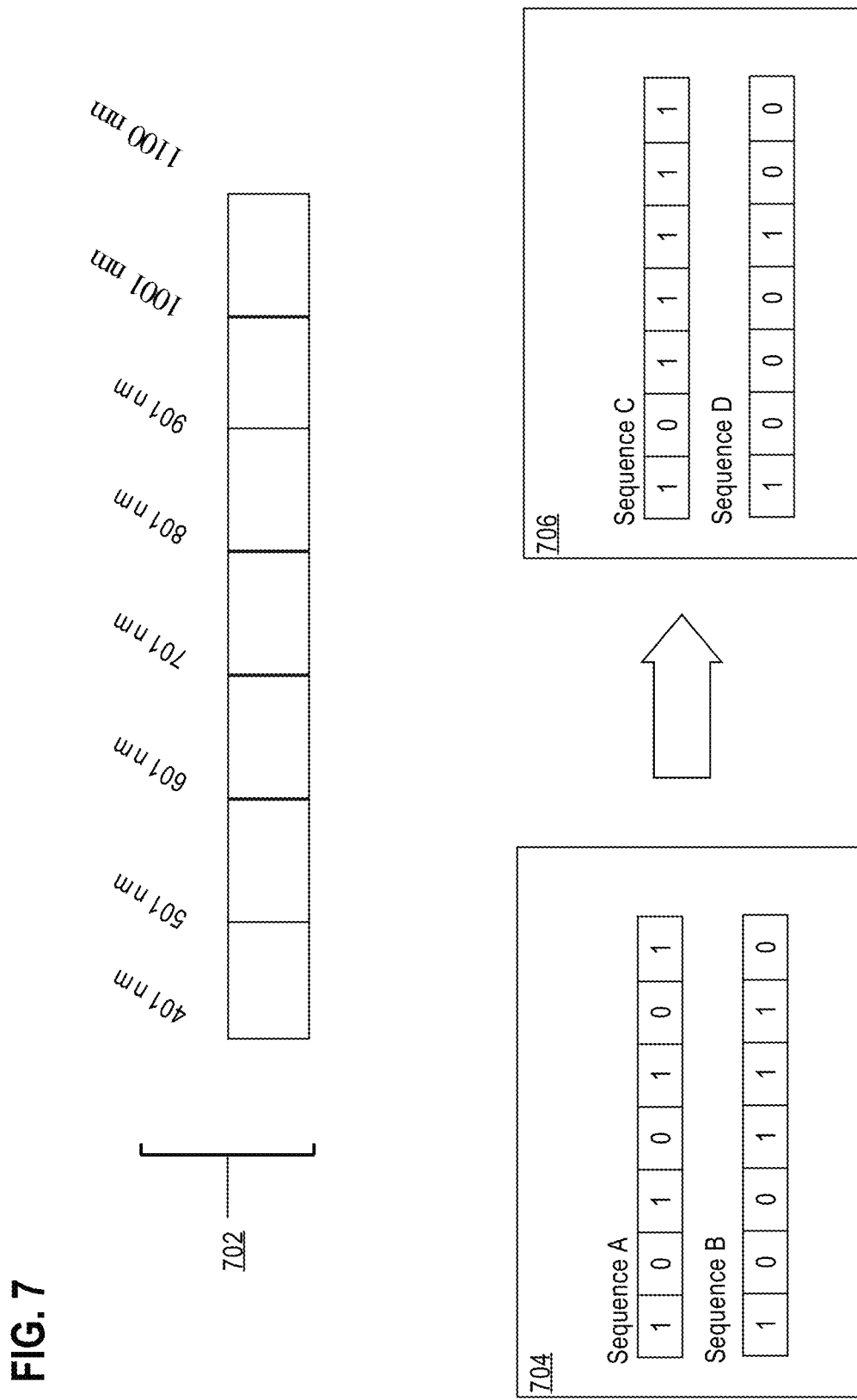
FIG. 7 illustrates a generating a pair of offset genetic sequences from a pair of population genetic sequences.

At step 604 the band selection module 175 generates an offspring set from the population set. The offspring set is derived from the population set and is considered as the next generation of the population set. The offspring set consists of a plurality of offset sequences. Offset sequences are created by exchanging properties between two randomly paired genetic sequences from the population set. The paired genetic sequences exchange properties by randomly assigning a binary value for each gene from one of the paired genetic. By doing so, the offspring set allows for new experimental conditions by mixing binary values corresponding to different chosen spectral bands. For example, FIG. 7 depicts the creation of two offset genetic sequences, C and D, from population sequences, A and B. Legend 702 depicts a sample genetic sequence consisting of 7 genes each, where each gene represents a 100 nm range starting from 401 nm and ending at 1100 nm. Box 704 shows the sequences for A and B, where A is "1010101" and B is "1001110". The creation of offspring from A and B involves randomly selecting a gene from either A or B to create offset sequences. Box 706 depicts two offset sequences where the genes making up C were randomly selected from A and B, and the genes making up D are the genes that were not selected for C. Here C ends up with a sequence of "1011111" and D ends up with a sequence of "1000100".

At step 606 the band selection module 175 creates a mutation set from the offspring set. A mutation set consists of the offset sequences from the offspring set, however mutations are applied to the genes that make up the offset sequences in order to simulate random disturbance. In an embodiment, the mutations to the offset sequences are random and may or may not affect each offset sequence in the mutation set. Since each gene is made up of spectral bands that each signify a specific wavelength range, the mutation may alter the wavelength range of a specific spectral band. For example, if a specific spectral band represented by gene X covers the range of 550 nm-650 nm, then the mutation may alter the spectral band to only cover 575 nm-650 nm. Alternatively, the mutation may alter gene X's coverage to include 550 nm-690 nm. In yet another embodiment, the mutation may alter gene X's coverage to include the ranges of 550 nm-600 nm and 620 nm-650 nm.

At step 608 the band selection module 175 selects a preferred subset of spectral combinations. The band selection module 175 evaluates sequences within the mutation set in order to select a subset of sequences that may lead to desirable soil property models. The mutation set is evaluated using criterion quantitatively defining whether particular spectral band combinations are preferable.

In an embodiment, the steps of creating a population set, an offspring set, a mutation set, and evaluating the mutation set may be repeated based on specific quality thresholds. Specific quality thresholds may be based on RMSECV values. In an embodiment, if the mutation set does not meet specific quality thresholds, then the mutation set may iteratively be reprocessed and new a new mutation set may be produced based upon repeating steps 604 and 606.

In an embodiment, the band selection module 175 may be programmed to use the all subset models method for determining specific spectral band combinations. The all subset models method is a technique that consists of first generating all possible soil spectral band combinations. Then evaluating soil models created using each of the possible spectral band combinations.

In another embodiment, the band selection module 175 may implement the sequential search method. The sequential search method is aimed at finding optimal subsets of spectral band combination by starting with an initial subset of variables, and then replacing one variable at a time in order to determine the optimal data model. In this context, the band selection module 175 would first start with an initial spectral band combination and then evaluate the soil model created from it. Then the band selection module 175 would replace one spectral band at a time and evaluate the created models in order to determine the optimal spectral band combination.

5.3 Soil Regression Module

The soil regression module 176 implements a process of determining signature spectral band combinations from soil spectral band combinations sent from either the soil preprocessing module 173 or the band selection module 175. In an embodiment, the soil regression module 176 receives spectral band combinations from the band selection module 175 for the purpose of creating a preconfigured soil model. In another embodiment, the soil regression module 176 receives spectral band combinations from the soil preprocessing module 173, and historical soil property measurements from ground truth for the purpose of predicting a set of properties within soil at a measured geo-location.

A signature spectral band combination is a combination that is most useful in predicting a certain soil property. Therefore the set of signature spectral band combinations may be used to predict a set of properties within the soil. The soil regression module 176 may implement multiple techniques to determine signature spectral bands including, but not limited to, a partial least-square regression algorithm, random forest algorithm, principal component regression, partial least squares, ridge regression, lasso regression, and decision tree statistical procedures.

In an embodiment, the soil regression module 176 implements a partial least-square regression modeling on the spectral band combinations received. Partial least-square regression (PLSR) is a method for modeling relations between sets of observed variables by means of latent variables. In an embodiment, observed variables may include measured soil spectral wavelengths from the spectral band combinations. Latent variables are high leverage orthogonal factors within the observed soil spectral variance. The high leverage orthogonal factors are characterized by matching the high leverage orthogonal factors to similar factors that describe the observed variance within measurements of corresponding dependent variables. The PLSR consists of eigen-decompositions of soil spectral matrix (X), soil properties matrix (Y), score matrices T and U together through a regression:

$$X = TP^T + E$$

$$Y = UQ^T + F$$

$$U = TB$$

where E and F are residual matrices, P and Q are the loading matrices and B is the regression coefficient. Score matrices T and U are datasets of potential latent variables extracted from matrices X and Y, where T is the scoring matrix for X and U is the scoring matrix for Y. T is then used predict the values in U, which is then used to construct predictions for values in the soil properties matrix Y. Each column of T and U is a pair of latent variables that are sequentially extracted through an iterative procedure, based upon the non-linear iterative partial least-squares algorithm.

The result of discovering latent variables helps explain the variation between soil spectral band combinations and soil properties. The results are a subset of models that define a customized set of signature spectral band combinations that may be used for soil prediction. In an embodiment, the set of signature spectral band combinations may include one or more bands that vary in size and weight when compared to other bands in the signature spectral band combination. For example, band A may be given higher weight than bands B and C in the signature spectral band combination.

In another embodiment, the soil regression module 176 implements a random forest algorithm. A random forest algorithm is an ensemble learning method for regression analysis that operates by constructing multiple decision trees during a training period and then outputs the class that is the mean regression of the individual trees. The mean regression consists of a result set of latent variables that explain the variation between soil spectral bands and soil properties.

In yet another embodiment, the soil regression module 176 implements principal component regression modeling on the spectral band combinations received. Principal component regression (PCR) is a multivariate regression analysis technique based upon principal component analysis. Principal component analysis is a statistical procedure that uses orthogonal transformation to convert a set of measured variables, in this context the soil spectral bands, into scores on latent variables, which are called the principal components. PCR then applies a linear regression model to the principal components in order to predict correlations between observed soil spectral bands and soil properties.

In yet another embodiment, the soil regression module 176 may implement ridge regression or lasso (least absolute shrinkage and selection operator) regression, where the observed variables include the soil spectral bands. Ridge regression and lasso regression are two different types of techniques for analyzing multiple regression data that suffers from collinearity. Collinearity is the existence of near-linear relationships among independent variables, which can create inaccurate estimates of regression coefficients. By implementing ridge or lasso regression the soil regression module 176 is able to introduce a degree of bias to regression estimates, thereby reducing possible errors in the predictions of soil properties.

In order to determine if the subset of models created by multivariate regression techniques described above are useful models for soil property prediction, each of the models are cross validated using soil data that have known soil properties. Cross validation involves evaluating the set of signature spectral band combinations used in each model by determining the correlation between the soil spectrum data from the signature spectral band combination and the soil properties. Techniques for evaluating prediction models include, but are not limited to, root mean square error, mean absolute error, and mean percentage error. Each evaluation technique may implement different types of cross validation methods including, but not limited to, leave-one-out cross validation, k-fold cross validation, and bootstrapping techniques.

In an embodiment, the soil regression module 176 implements root mean square of leave-one-out cross validation, where the soil property predictions are evaluated against soil samples physically collected and analyzed. In an embodiment, to determine whether the set of signature spectral band combinations are accurate for soil prediction, the set of signature spectral band combinations are cross validated. In an embodiment, the models that define each particular signature spectral band combination are compared in terms of the root mean square error of leave-one-out cross validation (RMSECV). RMSECV can cross validate selected models by comparing their predicted dataset values against the observed values from soil physically collected and analyzed. When applying RMSECV, each model is generated from soil spectrum data excluding one data point measurement. By excluding one data point measurement, the RMSECV can determine whether a specific model can accurately predict soil properties from the omitted data point. In an embodiment, soil regression module 176 is configured or programmed to compute RMSECV using instructions that implement the expression:

$$RMSECV = \sqrt{\frac{1}{n}\sum_{i=1}^{n}(y_i - \hat{y}_i)^2}$$

where n is the number of total observations, $y_i$ is the soil sample measured value, and $\hat{y}_i$ is the predicted value from the evaluated model. In an embodiment, a quality RMSECV score may vary depending upon the specific soil property predicted.

In another embodiment, the soil regression module 176 may implement a mean absolute error to evaluate the prediction models. Mean absolute error is used to measure how close soil property predictions are to actual measured soil properties. The mean absolute error is an average of the absolute errors between the prediction and the ground truth.

In another embodiment, the soil regression module 176 may implement a mean percentage error to evaluate the prediction models. Mean percentage error is used to compute the average of percentage errors between soil property predictions and actual values.

The soil regression module 176 may implement different validation methods in conjunction with the evaluation methods described above. Leave-one-out cross validation involves cross validating soil spectrum data using one dataset to validate the model created by the remaining datasets. K-fold cross validation is a cross validation technique where the original soil spectrum data measured is divided into k equal subsamples. Out of the k subsamples, one set is retained for validation purposes, while the remaining k−1 subsamples are used for model prediction. Bootstrapping is the practice of estimating properties of an estimator, which in this case the estimator is the created soil model. Those properties are cross validated by measuring those properties when sampling from an approximating distribution.

5.4 Local Soil Model

Preconfigured soil models are models that can be used to predict soil properties for multiple fields and can be constructed using hyperspectral data, without the need for physical soil samples. However, local soil models created with hyperspectral data and a set of physical soil samples may provide more accurate models tailored to a specific geo-location. A geo-location may include, but is not limited to, areas comprising land units measured in terms of acreages. A specific land unit may include different types of soil in different parts of the land unit. For example, the northwest portion of the land unit may contain very little organic matter and therefore have poor fertility levels, but the southeast portion of the land unit may have soil properties that make the soil very fertile. Preconfigured soil models constructed using hyperspectral sensors from satellites are unable to resolve soil properties and such a fine level and therefore tend to create models based upon the average spectral data for the entire land unit and surrounding land units. In order to create more accurate soil models for each land unit, soil data should be collected at proximity closer than satellites or other aerial vehicles.

In an embodiment, soil spectral data may be collected electronically using digital electronic sensors that are affixed to land vehicles or sensors that are part of portable devices.

Sensors, such as hyperspectral sensors attached to farming equipment, are able to capture and digitally store soil spectrum data at resolutions as fine as 10 meters or smaller because of their proximity to the soil. Unlike preconfigured soil models created using only hyperspectral data from satellites, more accurate local soil models may be created based upon soil spectrum data and physical soil samples collected from the geo-location of interest.

In an embodiment, physical soil samples are analyzed for their soil property makeup and are then correlated to the soil spectrum data using multivariate regression techniques, as described in the 5.3 SOIL REGRESSION MODULE section.

Collecting physical soil samples for a given land unit may be an expensive and time-consuming process. In order to efficiently collect and use the requisite number of physical soil samples for local soil model creation, soil sample collection techniques focus on obtaining a small set of soil samples that are representative of the full range of soil makeup for that given geo-location.

Figure 8:
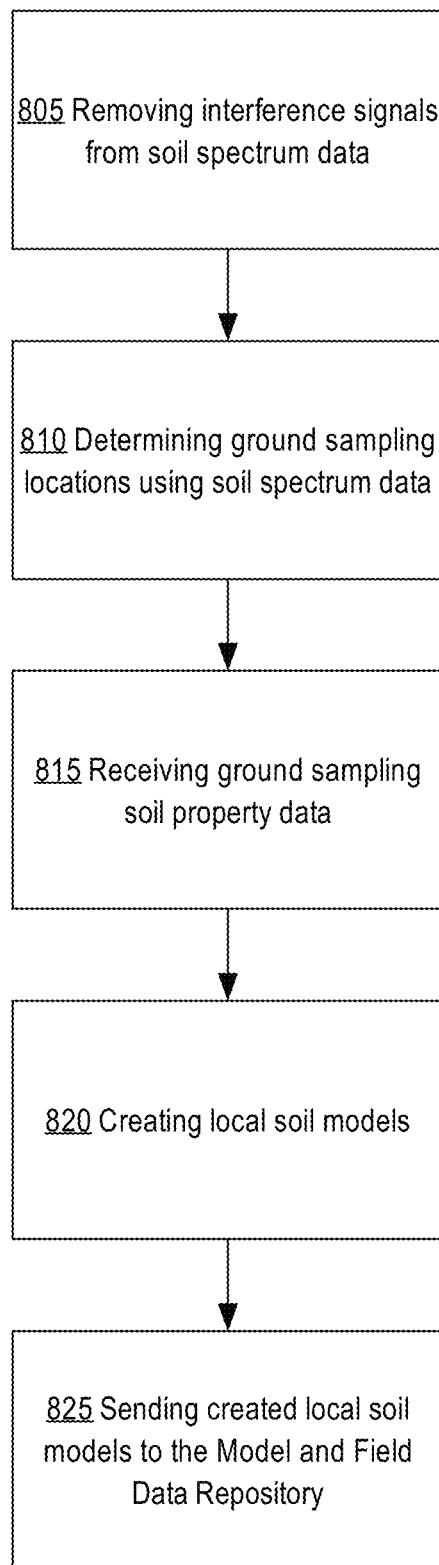
FIG. 8 illustrates a computer-implemented process for generating a localized soil model by receiving soil spectrum data, removing interference signals from the soil spectrum data, determining an optimal number of ground sample locations, and creating a local soil model or soil map based on ground samples and the subset of soil spectral bands.

FIG. 8 is a flow diagram that depicts an example computer implemented process for generating and calibrating one or more local soil models for a specific geo-location using soil spectrum data and one or more physically collected and analyzed soil samples. FIG. 8 may serve as an algorithm providing a basis for programming a computer including the soil preprocessing module described herein to execute the functions that are described in this section.

At step 805, the soil preprocessing module 173 removes interference signals from the received soil spectrum data for a specific land unit. For example, hyperspectral sensors attached to land vehicles are used to collect soil spectrum data by roving across the entire land unit. The collected soil spectrum data is processed by the soil preprocessing module 173. In an embodiment, the soil preprocessing module 173 receives: soil spectrum data; information pertaining to which type of sensor was used to collect the soil spectrum data; and at what elevation the soil spectrum data was captured. The purpose of receiving the sensor information and elevation data is to determine which preprocessing techniques need to be applied to the hyperspectral data in order to remove any interference signals.

At step 810, the spatial sampling module 172 determines ground sampling locations, within the specific land unit, using spatial sampling techniques on the received soil spectrum data. In an embodiment, spatial sampling techniques may include, but are not limited to, conditional Latin Hypercube Sampling. Conditional Latin Hypercube Sampling is used to determine specific locations within the land unit that provide a representative sampling of the entire soil range.

Latin Hypercube Sampling is a technique for generating a sampling of random variables from multivariate distributions. Conditional Latin Hypercube Sampling (cLHS) is a technique for generating a sampling of random variables that cover a range of values of each of the covariates by maximally stratifying marginal distribution. cLHS involves sampling a specified number of values "n" from a prescribed distribution of each of the covariates "$x_1, x_2, x_3 \ldots x_k$" where "k" is the number of covariates. The cumulative distribution for each covariate variable is then divided into "n" equiprobable intervals. A value is randomly selected from each equiprobable interval. The "n" values selected for each covariate variable are then matched randomly with values of the other covariate variables. Thus creating a multivariate distribution for X number of soil sampling sites that is maximally stratified.

Figure 9:
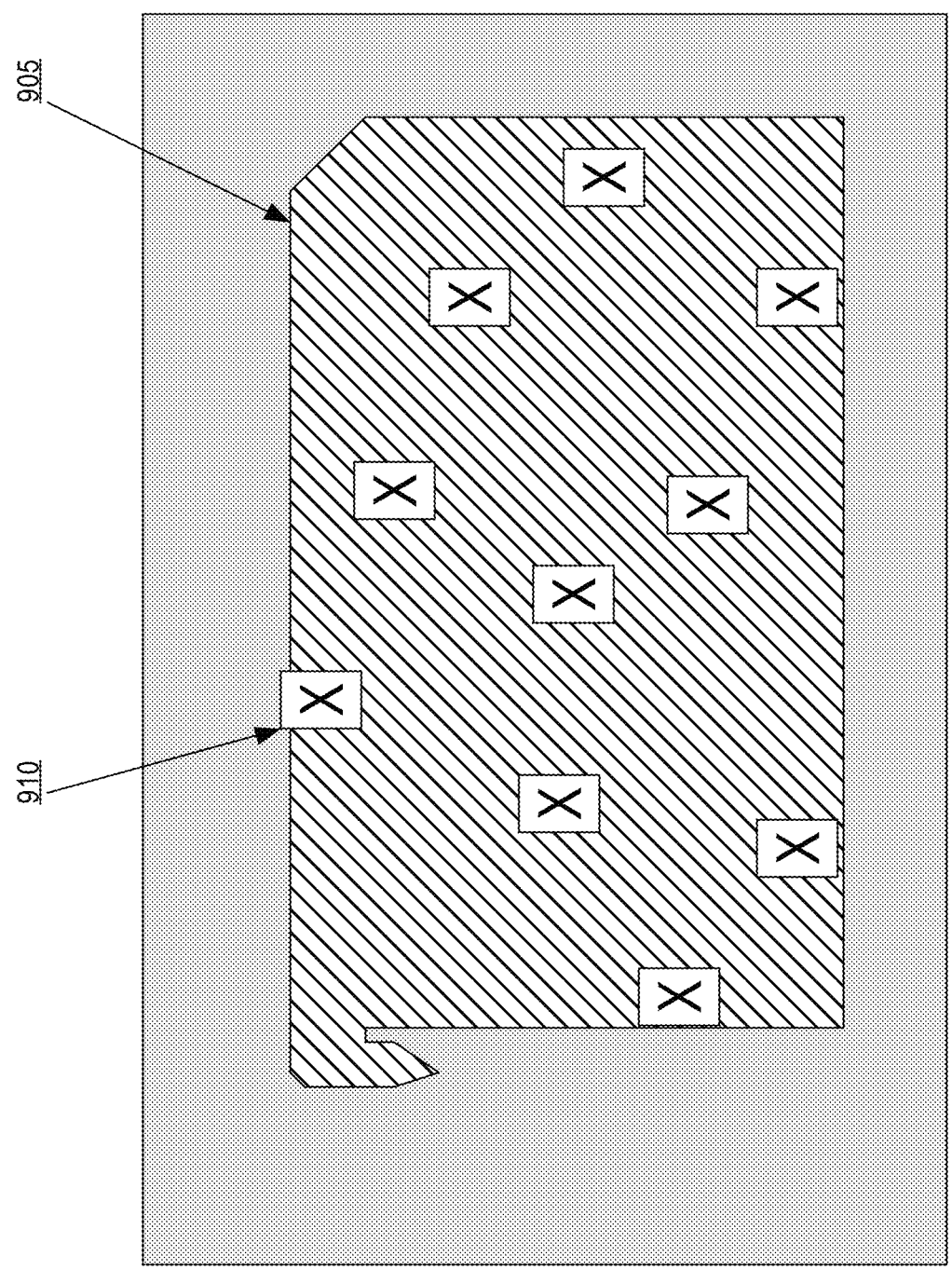
FIG. 9 illustrates an embodiment of a specific land unit and identified ground sample locations from which to extract ground samples.

FIG. 9 represents an embodiment of a specific land unit from which the spatial sampling module 172 determines sampling locations within the specific land unit. Land unit 905 represents a specific land unit. The land unit may be based upon identified common land units or may be based upon one or more identified farm acres. Soil sample site 910 depicts an example of multiple soil sites chosen within the land unit 605 for ground sample collection.

At step 815, the soil regression module 176 receives ground sampling soil property data from a source that physically collected the ground sample from the specified locations determined in step 810. In an embodiment, ground sampling soil property data consists of data that has been analyzed to determine specific levels of soil properties present at the specified ground sampling locations.

At step 820, the soil regression module 176 creates a local soil model using the received ground sampling soil property data to correlate specific soil properties to the soil spectrum data received from the soil preprocessing module 173. In an embodiment, the soil regression module 176 uses the identified soil properties from the ground sampling data to discover and calibrate latent variables during multivariate regression analysis and creates a local soil model. Further detail of multivariate regression is discussed in the section titled 5.3 SOIL REGRESSION MODULE.

At step 825, the soil regression module 176 stores the one or more created local soil modules in the model and field data repository 160. In an embodiment, the stored local soil model may be used to predict soil properties for the specific geo-location that the local soil model was based upon. In another embodiment, the stored local soil model may be used to train and calibrate one or more preconfigured soil models that cover a corresponding region or geo-location. The spatial sampling module 172 and/or the soil regression module 176 also can be programmed to determine optimal locations for planting, nutrient applications, scouting, or implementing sentinel seed technology for the purpose of determining intrafield properties related to crop yield and crop health. Output data relating to the optimal locations may be displayed, alone or with recommendation data, in a soil map.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A computer-implemented method for building and using soil models that determine soil properties from soil spectrum data, the method comprising:
   selecting, by a processor of a server computer system, a subset of a set of spectral bands of remotely sensed, soil spectrum data for an agricultural field;
   generating, by the processor, based on, at least in part, the subset of the set of spectral bands and soil property data obtained for the agricultural field, multiple soil models that correlate the subset of the set of spectral bands with the soil property data;

selecting, by the processor, one or more soil models, from the multiple soil models, based on cross validation of the one or more soil models satisfying a defined quality threshold;

based on the selected one or more soil models, generating one or more scripts for controlling one or more operating parameters of one or more agricultural machines; and transmitting the one or more scripts to the one or more agricultural machines to cause the one or more agricultural machines to use the one or more scripts to control the one or more operating parameters of the one or more agricultural machines to allow the one or more agricultural machines to perform agricultural operations at one or more location of the agricultural field.

2. The computer-implemented method of claim 1, further comprising receiving, by the processor, the remotely sensed, soil spectrum data from sensors affixed to movable equipment; and wherein the soil spectrum data are associated with different locations within the agricultural field.

3. The computer-implemented method of claim 2, further comprising:

prior to generating the multiple soil models, removing interference signals from the soil spectrum data, using a preprocessing technique selected from a plurality of preprocessing techniques, based on the soil spectrum data, a type of the sensors used to collect the soil spectrum data, or elevation at which the soil spectrum data are received.

4. The computer-implemented method of claim 3, wherein the plurality of preprocessing techniques comprises: data smoothing, spectral derivatives, standard normal variate preprocessing, or absorbance.

5. The computer-implemented method of claim 1, further comprising:

determining one or more ground sampling locations within the agricultural field based on the soil spectrum data; and using spatial sampling techniques on the soil spectrum data.

6. The computer-implemented method of claim 5, wherein the spatial sampling techniques include a conditional Latin Hypercube Sampling.

7. The computer-implemented method of claim 1, wherein generating multiple soil models comprises: discovering and calibrating latent variables during a multivariate regression analysis.

8. The computer-implemented method of claim 7, wherein the discovering and calibrating latent variables comprises: using one or more signature spectral band determination techniques of a partial least-square regression algorithm, a random forest algorithm, principal component regression, partial least squares, ridge regression, lasso regression, or decision tree statistical procedures.

9. The computer-implemented method of claim 1, further comprising: predicting soil properties for a specific geolocation within the agricultural field using the one or more soil models.

10. The computer-implemented method of claim 1, further comprising: determining optimal locations for planting, nutrient applications, scouting, or implementing sentinel seed technology using the one or more soil models.

11. The computer-implemented method of claim 10, further comprising: causing displaying the optimal locations in a soil map.

12. One or more non-transitory storage media storing instructions which, when executed by one or more computing devices, cause performance, by the one or more computing devices, of:

selecting a subset of a set of spectral bands of remotely sensed, soil spectrum data for an agricultural field;

generating, based on, at least in part, the subset of the set of spectral bands and soil property data obtained for the agricultural field, multiple soil models that correlate the subset of the set of spectral bands with the soil property data;

selecting one or more soil models, from the multiple soil models, based on cross validation of the one or more soil models satisfying a defined quality threshold;

based on the selected one or more soil models, generating one or more scripts for controlling one or more operating parameters of one or more agricultural machines; and transmitting the one or more scripts to the one or more agricultural machines to cause the one or more agricultural machines to use the one or more scripts to control the one or more operating parameters of the one or more agricultural machines to allow the one or more agricultural machines to perform agricultural operations at one or more location of the agricultural field.

13. The one or more non-transitory storage media of claim 12, wherein the instructions, when executed by the one or more computing devices, cause performance, by the one or more computing devices, of receiving the remotely sensed, soil spectrum data from sensors that are affixed to movable equipment; and wherein the soil spectrum data are associated with different locations within the agricultural field.

14. The one or more non-transitory storage media of claim 13, wherein the instructions, when executed by the one or more computing devices, further cause performance, by the one or more computing devices, of removing interference signals from the soil spectrum data through a preprocessing technique of a plurality of preprocessing techniques, based on the soil spectrum data, a type of the sensor used to collect the soil spectrum data, or elevation at which the soil spectrum data are received.

15. The one or more non-transitory storage media of claim 14, wherein the plurality of preprocessing techniques comprises: data smoothing, spectral derivatives, standard normal variate preprocessing, or absorbance.

16. The one or more non-transitory storage media of claim 12, wherein the instructions, when executed by the one or more computing devices, further cause performance, by the one or more computing devices, of determining ground sampling locations within the agricultural field based on updated soil spectrum data; and using spatial sampling techniques on the updated soil spectrum data.

17. The one or more non-transitory storage media of claim 16, wherein the spatial sampling techniques include conditional Latin Hypercube Sampling.

18. The one or more non-transitory storage media of claim 12, wherein the instructions, when executed by the one or more computing devices, cause performance, by the one or more computing devices, in connection with generating the multiple models, of discovering and calibrating latent variables during a multivariate regression analysis.

19. The one or more non-transitory storage media of claim 18, wherein the instructions, when executed by the one or more computing devices, cause performance, by the one or more computing devices, in connection with discovering and calibrating latent variables, of using one or more signature spectral band determination techniques of a partial least-square regression algorithm, a random forest algorithm, principal component regression, partial least squares, ridge regression, lasso regression, or decision tree statistical procedures.

\* \* \* \* \*